US008263560B2

(12) United States Patent
Strome et al.

(10) Patent No.: US 8,263,560 B2
(45) Date of Patent: Sep. 11, 2012

(54) HPV 16 PEPTIDE VACCINE FOR HEAD AND NECK CANCER

(75) Inventors: Scott E. Strome, Reisterstown, MD (US); Esteban Celis, Tampa, FL (US)

(73) Assignees: University of Maryland Baltimore, Baltimore, MD (US); Mayo Foundation for Medical Education and Research, Rochester, MN (US)

( * ) Notice: Subject to any disclaimer, the term of this patent is extended or adjusted under 35 U.S.C. 154(b) by 576 days.

(21) Appl. No.: 11/837,737

(22) Filed: Aug. 13, 2007

(65) Prior Publication Data

US 2008/0044407 A1    Feb. 21, 2008

Related U.S. Application Data

(63) Continuation of application No. 11/391,632, filed on Mar. 29, 2006, now abandoned.

(60) Provisional application No. 60/667,060, filed on Apr. 1, 2005.

(51) Int. Cl.
*A61K 38/16* (2006.01)
*A61P 31/00* (2006.01)

(52) U.S. Cl. ..................... 514/21.3; 514/19.3

(58) Field of Classification Search .................. None
See application file for complete search history.

(56) References Cited

U.S. PATENT DOCUMENTS

| | | | |
|---|---|---|---|
| 4,867,973 A | 9/1989 | Goers et al. | |
| 5,662,907 A | 9/1997 | Kubo et al. | |
| 5,846,827 A | 12/1998 | Celis et al. | |
| 5,965,535 A | 10/1999 | Chaux et al. | |
| 6,037,135 A | 3/2000 | Kubo et al. | |
| 6,419,931 B1 | 7/2002 | Vitiello et al. | |
| 6,534,482 B1 | 3/2003 | Fikes et al. | 514/44 |
| 6,602,510 B1 | 8/2003 | Fikes et al. | |
| 6,602,705 B1 | 8/2003 | Barnett et al. | 435/320.1 |
| 6,686,147 B1 | 2/2004 | Scanlan et al. | |
| 6,689,363 B1 | 2/2004 | Sette et al. | |
| 6,794,501 B2 | 9/2004 | Chen et al. | |
| 7,026,443 B1 | 4/2006 | Sette et al. | 530/300 |
| 7,049,413 B2 | 5/2006 | Zhang et al. | |
| 7,252,829 B1 | 8/2007 | Sette et al. | |
| 2004/0053822 A1 | 3/2004 | Fikes et al. | |
| 2004/0054137 A1 | 3/2004 | Thomson | |
| 2004/0249126 A1 | 12/2004 | Celis | |
| 2007/0014810 A1 | 1/2007 | Baker et al. | |
| 2007/0053922 A1 | 3/2007 | Sette et al. | |
| 2007/0055049 A1 | 3/2007 | Grey et al. | |

FOREIGN PATENT DOCUMENTS

| | | |
|---|---|---|
| WO | WO97/33602 | 9/1997 |
| WO | WO99/45954 | 9/1999 |
| WO | WO99/61916 | 12/1999 |
| WO | WO00/52045 | 9/2000 |
| WO | WO01/42267 | 6/2001 |
| WO | WO01/90197 | 11/2001 |
| WO | WO03/000907 | 1/2003 |
| WO | WO03/040165 | 5/2003 |
| WO | WO2005/037190 | 4/2005 |
| WO | WO2005/089164 | 9/2005 |
| WO | WO2006/091734 | 8/2006 |
| WO | WO2006/106435 | 10/2006 |
| WO | WO2006/113622 | 10/2006 |

OTHER PUBLICATIONS

Lu et al (The Journal of Immunology v172 2004 pp. 4575-4582).*
Baldwin et al (Clinical Cancer Research v9 2003 pp. 5205-5213).*
Van der Burg et al (Int J Cancer v91 2001 pp. 612-618).*
U.S. Appl. No. 09/350,401, filed Jul. 8, 1999, IDM Pharma.
U.S. Appl. No. 10/387,336, filed Mar. 11, 2003, Chiron.
U.S. Appl. No. 10/654,601, filed Sep. 4, 2003, Epimmune.
U.S. Appl. No. 10/817,970, filed Apr. 6, 2004, Cytel Corp.
U.S. Appl. No. 11/045,024, filed Jan. 28, 2005, Cytel Corp.
U.S. Appl. No. 11/051,411, filed Feb. 7, 2005, IDM Pharma.
U.S. Appl. No. 11/100,356, filed Apr. 6, 2005, Chiron.
U.S. Appl. No. 11/418,504, filed May 5, 2006, IDM Pharma.
U.S. Appl. No. 11/474,521, filed Jun. 23, 2006, Celis.
U.S. Appl. No. 11/482,832, filed Jul. 10, 2006, Fikes.
U.S. Appl. No. 11/522,314, filed Sep. 18, 2006, Epimmune.
Tang et al., "The Carboxyl Terminus of RNA Helicase A Contains a Bidirectional Nuclear Transport Domain," Mol. Cell Biol., 19(5), pp. 3540-3550.
Final Rejection mailed Mar. 30, 2007 in Co-Pending U.S. Appl. No. 11/391,632.
Preliminary Amendment filed Apr. 7, 2010 in Co-Pending U.S. Appl. No. 12/696,385.
Tang et al., "The Carboxyl Terminus of RNA Helicase A Contains a Bidirectional Nuclear Transport Domain," Mol. Cell Biol., 19(5), pp. 3540-3550, 1999.
Gil-Torregrosa et al., "Major Histocompatibility Complex Class I Viral Antigen Processing in the Secretory Pathway Defined by the *trans*-Golgi Network Protease Furin," J. Exp. Med. 1998, 188(6), pp. 1105-1116.
Kim et al., "Introduction of Soluble Proteins into the MHC Class I Pathway by Conjugation to an HIV *tat* Peptide," J. Immunol., 1997, 159, pp. 1666-1668.
Ishioka et al., "Utilization of MHC Class I Transgenic Mice for Development of Minigene DNA Vaccines Encoding Multiple HLA-Restricted CTL Epitopes," J. Immunol., 1999, 162, pp. 3915-3925.
Lees et al., "The effect of T1 and T2 Cytokines on the Cytotoxic T Cell Response to Mannan-MUC1," Cancer Immunol. Immunother., 2000, 48(11), pp. 644-652 (abstract only).
Heuser et al., "An anti-MUC1-antibody-interleukin-2 Fusion Protein that Activates Resting NK Cells to Lysis of MUC1-Positive Tumour Cells," Br. J. Cancer, 2003, 89, 1130-1139.

* cited by examiner

*Primary Examiner* — Cecilia J Tsang
*Assistant Examiner* — Ronald Niebauer
(74) *Attorney, Agent, or Firm* — Cooley LLP

(57) ABSTRACT

The present invention relates to Trojan antigens, and immunogenic compositions comprising the Trojan antigens. The present invention also relates to methods of generating an immune response in a subject using the Trojan antigens or immunogenic compositions. The present invention further relates to methods of treating squamous cell carcinoma of the head and neck (SCCHN) using the Trojan antigens and immunogenic compositions of the present invention.

15 Claims, 5 Drawing Sheets

HPV 16 PEPTIDE VACCINE FOR HEAD AND NECK CANCER

This is a continuation of Application No. 11/391,632, filed Mar. 29, 2006 now abandoned, which claims benefit of U.S. provisional application No. 60/667,060, filed Apr. 1, 2005, the contents of which are incorporated herein by reference in their entirety.

This invention was made with U.S. Government support under grant number 5R01DE015324-04, awarded by the National Institute of Dental and Craniofacial Research, National Institutes of Health. The U.S. Government has certain rights in this invention.

BACKGROUND OF THE INVENTION

Squamous cell carcinoma of the head and neck (SCCHN) effects 43,000 individuals in the United States annually with an estimated 5-year overall survival of 50% (R. M. Byers, Dr. Martin: How are we doing in 2000? *Archives of Otolaryngology-Head and Neck Surgery* 127:759-765 (2001)). For some patients who develop local or distant metastases following primary therapy, surgical salvage is a viable therapeutic option. The remainder of individuals is forced to choose between palliative chemotherapy and supportive care. In order to improve both survival and quality of life for patients with unresectable disease, new therapeutic alternatives are mandated.

One treatment option is the use of T cell-specific immunotherapy to stimulate a patient's anti-tumor immune response. Several T cell based strategies have demonstrated clinical efficacy for the treatment of unresectable tumors of diverse histologic types (Kugler et al. Regression of human metastatic renal cell carcinoma after vaccination with tumor cell-dendritic cell hybrids. *Nature Medicine* 6(3):332-6 (2000); Nestle et al. Vaccination of melanoma patients with peptide- or tumor lysate-pulsed dendritic cells. *Nature Medicine* 4(3): 328-32 (1998); Rosenberg et al. Immunologic and therapeutic evaluation of a synthetic peptide vaccine for the treatment of patients with metastatic melanoma. *Nature Medicine* 4(3): 321-327 (1998)). However, the majority of trials have failed to demonstrate any therapeutic benefit (Chang et al. A phase I trial of tumor lysate-pulsed dendritic cells in the treatment of advanced cancer. *Clinical Cancer Research* 8(4):1021-1032 (2002)). The causes of these failures are multi-factorial, but are likely related to well characterized immunologic defects within the target population, including aberrant antigen processing and presentation, which restrict T cell function. Specifically, tumor bearing patients have demonstrable defects in antigen presentation, both at the tumor cell and professional antigen presenting cell (APC) levels, e.g., down regulation of TAP and HLA molecules, which, in some cases, can be overcome by the administration of interferon (Seliger et al. Antigen-processing machinery breakdown and tumor growth. *Immunology Today* 21(9):455-64 (2000); Marincola et al. Escape of human solid tumors from T-cell recognition: Molecular mechanisms and functional significance, *Advanced Immunology* 74:181-273 (2000)). Additionally, in cancer patients T cells are found to be tolerized or improperly activated which might be caused by down regulation of the zeta chain of the T cell receptor (TCR) and P56LCK signaling molecule (Mizoguchi et al. Alterations in signal transduction molecules in T lymphocytes from tumor-bearing mice. *Science* 258(5089):1795-8 (1992)).

Classic experiments by Gross in the 1940s created the foundation for the field of tumor immunology, demonstrating that C3H mice capable of rejecting a syngeneic murine sarcoma developed protective immunity to subsequent injections of the same tumor, but not to a spontaneously arising murine mastocytoma (L. Gross, Intradermal immunization of C3H mice against a sarcoma that originated in an animal of the same line. *Cancer Res.* 326-333 (1943)). This immune response is directed against tumor specific target antigens and is cellular in nature as lymphocytes, but not serum, from previously immunized animals are effective in lysing tumor (Prehn et al. Immunity to methylcolanthrene-induced sarcomas. *Journal of the National Cancer Institute* 6:769-778 (1957).

It is now clear that tumor antigens are presented in the context of specific class I and class II HLA molecules. Class I presentation, in the presence of appropriate costimulation, is thought to stimulate a cytolytic CD8+ T cell response, while antigen presentation in the context of class II molecules is postulated to stimulate a CD4+ helper T cell response (Townsend et al., Antigen recognition by class I-restricted T lymphocytes. *Annual Review of Immunology* 7:601-624 (1989)). Tumors can evade the immune response by manipulating these antigen presentation pathways. Specifically, direct tumor presentation of antigen in the absence of costimulation results in T cell anergy (D. M. Pardoll, Cancer vaccines. *Nature Medicine* 4(5 supp):525-531 (1998)). Additionally, down regulation of either HLA molecules on the tumor surface or tumor antigen expression limits the efficacy of antigen-specific cytotoxic T cells (Seliger et al. Antigen-processing machinery breakdown and tumor growth. *Immunology Today* 21(9):455-64 (2000)). Finally, tumors can upregulate non-classical HLA molecules, e.g., HLA G, which are thought to suppress T cell anti-tumor immunity (Rouas-Freiss et al. HLA-G promotes immune tolerance. *Journal of Biological Regulators & Homeostatic Agents* 14(2):93-8 (2000)). These molecular methods of protection provide clear evidence that CTLs induce selective pressure on tumors and can potentially be harnessed with therapeutic intent.

Several strategies have been employed to prime the anti-tumor T cell response. A major advance in the field of immunotherapy is the clinical application of a class of professional antigen presenting cells (APC), termed dendritic cells (DC), into clinical trials. Dendritic cells are thought to stimulate the T cell anti-tumor response by the presentation of tumor associated antigens in the context of class I and II MHC, co-stimulatory molecules, and appropriate chemokines/cytokines (Gilboa et al. Immunotherapy of cancer with dendritic-cell-based vaccines. *Cancer Immunology, Immunotherapy* 46(2):82-7 (1998)). Presentation of putative tumor antigens by DC is postulated to effectively overcome tumor induced tolerance (Dallal et al. The dendritic cell and human cancer vaccines, *Current Opinion in Immunology* 12(5):583-8 (2000)). This suggests that vaccine approaches using DC primed with tumor specific antigens will be an effective means to stimulate tumor specific immunity.

Recent evidence suggests that DC primed with tumor-associated antigens in the form of peptides, tumor lysates, or tumor RNA are capable of mediating a potent anti-tumor immune response (Nair et al. Regression of tumors in mice vaccinated with professional antigen-presenting cells pulsed with tumor extracts. *International Journal of Cancer* 70(6): 706-15 (1997)). While ex vivo maturation of DC is one method of priming DC, such maturation is expensive and can lack reproducibility. Specifically, because large numbers of DC are required for vaccine preparation, 1-2 leukophoreses are often required.

One means to potentially eliminate problems associated with ex vivo maturation is through the use of DC stimulation in vivo. Monocytes cultured in appropriate concentrations of IL-4 and GM-CSF transform into immature DC (Banchereau et al. Dendritic cells and the control of immunity. *Nature* 392(6673):245-52 (1998); R. M. Steinman, The dendritic cell system and its role in immunogenicity. *Annual Review of Immunology* 9:271-96 (1991)). GM-CSF is the critical component for stimulating DC maturation, phagocytosis, migration, and HLA class II expression (J. O. Armitage. Emerging applications of recombinant human granulocyte-macrophage colony-stimulating factor. *Blood* 92(12):4491-508 (1998)). The majority of clinical trials have cultured DC precursors in recombinant GM-CSF, with subsequent administration back to the host as part of a tumor vaccine. Recent data from Disis et al. demonstrates that the presentation of tumor peptides in a rat model is enhanced by subcutaneous or intradermal administration of GM-CSF (Disis et al. Granulocyte-macrophage colony-stimulating factor: an effective adjuvant for protein and peptide-based vaccines. *Blood* 88(1):202-10 (1996)). The concept of in vivo administration of GM-CSF in combination with an autologous vaccine has been clinically evaluated in patients with advanced melanoma. Specifically, using an autologous melanoma vaccine in combination with GM-CSF and BCG, Leong et al. demonstrated a 10% complete response rate with an equal number of partial responders in a cohort of 20 patients (Leong et al. Recombinant human granulocyte macrophage-colony stimulating factor (rhGM-CSF) and autologous melanoma vaccine mediate tumor regression in patients with metastatic melanoma. *Journal of Immunotherapy* 22(2):166-74 (1999)). Using a modification of this approach, Soiffer et al. demonstrated that a vaccine composed of irradiated melanoma cells engineered to secrete GM-CSF, stimulated T cell mediated tumor destruction in 11/16 patients (Soiffer et al. Vaccination with irradiated autologous melanoma cells engineered to secrete human granulocyte-macrophage colony-stimulating factor generates potent antitumor immunity in patients with metastatic melanoma. *PNAS* 95(22):13141-13146 (1998)). Finally, Bendandi et al. demonstrated molecular remission of residual lymphoma in 8/11 patients after treatment with an idiotype protein vaccine in combination with either 100 or 500 ug/M2 of GM-CSF (Bendandi et al. Complete molecular remissions induced by patient-specific vaccination plus granulocyte-monocyte colony-stimulating factor against lymphoma. *Nature Medicine* 5(10):1171-7 (1999)). Importantly, in this trial the vaccine was given once per month for four cycles with a booster given 2 months after the final cycle. GM-CSF was given at the time of vaccination and daily, for three additional doses. These data suggest that in vivo administration of GM-CSF may supplant the need for in vitro culture of DC precursors.

Additional problems with whole tumor based approaches include the potential for tumor contamination, small cell number, and limited ability to monitor the immune response. An alternative approach is the use of tumor associated synthetic antigens for immunologic priming. Peptide-based strategies for DC priming enable prior characterization of the immunologic stimulant, facilitating subsequent analysis of the anti-tumor immune response. Because specific peptides are ubiquitous in tumors of the same histologic type, identical peptide vaccines may be employed in allogeneic hosts bearing the same tumor histology. Additionally, the use of single peptides for immunization limits the potential induction of undesired autoimmunity (Nestle et al. Vaccination with melanoma patients with peptide- or tumor lysate-pulsed dendritic cells. *Nature Medicine* 4(3):328-32 (1998); Tsai et al. In vitro immunization and expansion of antigen-specific cytotoxic T lymphocytes for adoptive immunotherapy using peptide-pulsed dendritic cells. *Critical Reviews in Immunology* 18(1-2):65-75 (1998); Tsai et al. Identification of subdominant CTL epitopes of the GP100 melanoma-associated tumor antigen by primary in vitro immunization with peptide-pulsed dendritic cells. *Journal of Immunology* 158(4):1796-1802 (1997)). Finally, recent developments in the use of soluble MHC Class I peptide tetramers/dimers and Elispot technology have enabled rapid characterization of epitope specific CTL response (Altman et al. Phenotypic analysis of antigen-specific T lymphocytes. *Science* 274(5284):94-96 (1996); V. Cerundolo. Use of major histocompatibility complex class I tetramers to monitor tumor-specific cytotoxic T lymphocyte response in melanoma patients. *Cancer Chemotherapy & Pharmacology* 46(Suppl):S83-5 (2000)). The primary limitations to peptide-based vaccine strategies are haplotype restriction; potential for degradation; the lack of identifiable putative tumor antigens recognized to induce a CTL response; the potential failure of the efferent arm of the immune response if smaller numbers of peptides are employed; and uncertainty regarding which peptides, used alone or in combination, are the most immunogenic (Nair et al. Regression of tumors in mice vaccinated with professional antigen-presenting cells pulsed with tumor extracts. *International Journal of Cancer* 70(6):706-15 (1997); Amoscato et al. Rapid extracellular degradation of synthetic class I peptides by human dendritic cells. *Journal of Immunology* 161 (8):4023-32 (1998)).

The optimal antigenic target is derived from a protein which is essential for cell survival, is expressed on all tumor cells, is tumor specific, is a surface protein, and is not expressed in the thymus nor during fetal development. No protein identified to date satisfies all of these criteria with regard to SCCHN tumors. However, several proteins have been identified with peptide epitopes capable of stimulating antigen specific CTL against SCCHN including SART1, SART 3, CASP8, and SCCA 1 (Hamada et al. Molecular cloning of human squamous cell carcinoma antigen 1 gene and characterization of its promoter, *Biochimica et Biophysica Acta* 1518(1-2):124-31 (2001); Nakao et al. Identification of a gene coding for a new squamous cell carcinoma antigen recognized by the CTL. *Journal of Immunology* 164 (5):2565-74 (2000); Shichijo et al. A gene encoding antigenic peptides of human squamous cell carcinoma recognized by cytotoxic T lymphocytes. *J. of Exp. Med.* 187(3):277-88 (1998); Yang et al. Identification of a gene coding for a protein possessing shared tumor epitopes capable of inducing HLA-A24-restricted cytotoxic T lymphocytes in cancer patients. *Cancer Research* 59(16):4056-63 (1999)). The major limitations to clinical application of these peptide epitopes are both their limited prevalence in SCCHN and putative epitopes restricted by HLA types with low population specific frequencies. For example, while SART-1 is expressed in the majority of SCCHN, the defined peptide epitopes are HLA26 restricted, limiting potential therapeutic application (Shichijo et al. A gene encoding antigenic peptides of human squamous cell carcinoma recognized by cytotoxic T lymphocytes. *J. of Exp. Med.* 187(3):277-88 (1998)). In order to increase therapeutic application, proteins should optimally be expressed in the majority of SCCHN, with defined epitopes representative of common HLA haplotypes.

One attractive candidate antigenic target for use in treating SCCHN is the MAGE-A3 differentiation antigen (SEQ ID NO: 27) initially identified in the human MZ2E melanoma (van der Bruggen et al. A gene encoding an antigen recognized by cytolytic T lymphocytes on a human melanoma. *Science* 254(5038):1643-7 (1991)). This protein is a member of the cancer testis family and is expressed on tumors of diverse histologic types. MAGE-A3 has high potential utility for the immunotherapy of SCCHN based on its tumor specificity, high percent expression, and the existence of previously defined epitopes. A recent report demonstrated the presence of MAGE-A3 in 44.4% of freshly isolated SCCHN by PCR and in 27% of specimens by immunohistochemistry (Kienstra et al. Identification of NY-ESO-1, MAGE-1, and MAGE-3 in head and neck squamous cell carcinoma. *Head and Neck* 25(6):457-463 (2003)). Additionally, HLA-A2 epitopes have been identified and clinically evaluated for the treatment of gastrointestinal malignancies and melanomas. Specifically, Sadanaga et al. utilized DC pulsed with the FLWGPRALV peptide (SEQ ID NO:1), restricted to the HLA-A2 epitope (van der Bruggen et al. A peptide encoded by human gene MAGE-3 and presented by HLA-A2 induces cytolytic T lymphocytes that recognize tumor cells expressing MAGE-3. *European Journal of Immunology* 24(12):3038-43 (1994)), and demonstrated the induction of CTL in 2/5 patients, with 2/6 patients enjoying a mixed clinical response (Sadanaga et al. Dendritic cell vaccination with MAGE peptide is a novel therapeutic approach for gastrointestinal carcinomas. *Clinical Cancer Research* 7(8): 2277-2284 (2001)). In a similar study in patients with metastatic melanoma, patients were vaccinated with PBMC pulsed with either MAGE-A3 or MelanA peptides in combination with IL-12. In eight patients who demonstrated an increased immune response, there was one complete response, one partial response, one minor response, and two mixed responses. Interestingly, in the mixed responders, tumor specimens that did not respond to treatment did not express the antigen used for vaccination (Gajewski et al. Immunization of HLA-A2+ melanoma patients with MAGE-3 or MelanA peptide-pulsed autologous peripheral blood mononuclear cells plus recombinant human interleukin 12. *Clinical Cancer Research* 7(3 Suppl):895s-901s (2001)).

Recently, a new peptide epitope of MAGE-A3, KVAELVHFL (SEQ ID NO:2), has been defined (Kawashima et al. The multi-epitope approach for immunotherapy for cancer: identification of several CTL epitopes from various tumor-associated antigens expressed on solid epithelial tumors. *Human Immunology* 59(1):1-14 (1998)). Dendritic cells pulsed with this peptide stimulate naive CTL to lyse MAGE-A3 positive tumors with an HLA-A2.1 phenotype. Although this peptide has not been clinically evaluated, studies suggest that it is capable of stimulating a higher percentage of tumor reactive CTL than FLWGPRALV.

In addition to class I epitopes, immunogenic HLA-DR restricted class II epitopes have also been defined for MAGE-A3. Specifically, Chaux et al. have identified an HLA-DR13 MAGE-A3$_{114-127}$ epitope AELVHFLLLKYRAR (SEQ ID NO:3), recognized by epitope specific HTL clones (Chaux et al. Identification of MAGE-3 epitopes presented by HLA-DR molecules to CD4(+) T lymphocytes. *Journal of Experimental Medicine* 189(5):767-778 1999)). Similarly, Manici et al. used a bioinformatics based approach to characterize 3 MAGE-A3 epitopes for HLA-DR11, MAGE-A3$_{281-295}$, MAGE-A3$_{141-155}$, and MAGE-A3$_{146-160}$. T cells stimulated with MAGE-A3$_{281-295}$, TSYVKVLHHMVKISG (SEQ ID NO:4), were capable of lysing HLA-DR11/MAGE-A3 positive melanomas (Manici et al. Melanoma cells present a MAGE-3 epitope to CD4(+) cytotoxic T cells in association with histocompatibility leukocyte antigen DR11. *Journal of Experimental Medicine* 189(5):871-876 (1999)). Additional recent evaluations by the present inventors demonstrated MAGE-A3$_{146-160}$ (VIFSKASSSLQL; SEQ ID NO:5) can stimulate T-helper cells restricted by both HLA-DR4 and HLA-DR7. MAGE-A3$_{146-160}$ is naturally processed, as peptide stimulated T cells react with DC primed with whole tumor preparations (Kobayashi et al. Tumor-reactive T helper lymphocytes recognize a promiscuous MAGE-A3 epitope presented by various major histocompatibility complex class II alleles. *Cancer Research* 61(12):4773-8 (2001)). Based on these two studies, it is clear that MAGE-A3$_{146-160}$ is naturally processed peptide epitope and that it is promiscuous for multiple HLA-DR epitopes, making it an ideal candidate for therapeutic application.

A second attractive candidate for peptide-based immunotherapy is the human papilloma virus (HPV) 16 E7 nuclear protein (SEQ ID NO:28). HPV 16 E7 protein is a tumor rejection antigen, which is postulated to play an integral role in the development of carcinoma of the uterine cervix. Recent studies by the present inventors, as well as others, have identified HPV 16 as an independent risk factor for oropharyngeal SCC (Strome et al. Squamous Cell Carcinoma of the Tonsils: A Molecular Analysis of HPV Associations, *Clinical Cancer Research* 18:1093-1100 (2002); Gillison et al. Evidence for a casual association between human papillomavirus and a subset of head and neck cancers. *Journal of the National Cancer Institute* 92:709-720 (2000); Gillison et al. Human papillomavirus in head and neck squamous cell carcinoma: are some head and neck cancers a sexually transmitted disease? *Current Opinion in Oncology* 11:191-199 (1999)). While a cause effect relationship remains to be established, several in vitro studies suggest that continued expression of the nuclear E6 and E7 proteins is likely required for malignant transformation of infected cells (Crook et al. Continued expression of HPV-16 E7 protein is required for maintenance of the transformed phenotype of cells co-transformed by HPV-16 plus EJ-ras. *EMBO Journal* 8(2):513-9 (1989); Munger et al. The E6 and E7 genes of the human papillomavirus type 16 together are necessary and sufficient for transformation of primary human keratinocytes. *Journal of Virology* 63(10): 4417-21 (1989)). Because of its association with malignancies of diverse histologic types, development of HPV-based peptide immunotherapy platforms can potentially impact the treatment of multiple disease entities.

Several groups have now identified HLA-A2 and HLA-DR restricted antigenic epitopes for the HPV 16 E7 nuclear protein (Feltkamp et al. Vaccination with cytotoxic T lymphocyte epitope-containing peptide protects against a tumor induced by human papillomavirus type 16-transformed cells. *European Journal of Immunology* 23(9):2242-2249 (1993); Feltkamp et al. Cytotoxic T lymphocytes raised against a subdominant epitope offered as a synthetic peptide eradicate human papillomavirus type 16-induced tumors. *European Journal of Immunology* 25(9):2638-42 (1995); Chen et al. Human papillomavirus type 16 nucleoprotein E7 is a tumor rejection antigen. *PNAS USA* 88(1):110-4 (1991); Nijman et al. Characterization of cytotoxic T lymphocyte epitopes of a self-protein, p53, and a non-self-protein, influenza matrix: relationship between major histocompatibility complex peptide binding affinity and immune responsiveness to peptides. *Journal of Immunotherapy* 14(2):121-6 (1993)). Two of these epitopes, E7 12-20 (MLDLQPETT; SEQ ID NO:6) and E7 86-93 (TLGIVCPI; SEQ ID NO:7), have been evaluated in phase I trials for cervical carcinoma. Treatment of 18 women who were HLA-A2 positive with high-grade cervical intraepithelial neoplasia with this regimen resulted in 3 complete responses and 6 partial responses (Nijman et al. Characterization of cytotoxic T lymphocyte epitopes of a self-protein, p53, and a non-self-protein, influenza matrix: relationship between major histocompatibility complex peptide binding affinity and immune responsiveness to peptides. *Journal of Immunotherapy* 14(2):121-6 (1993); Muderspach et al. A phase I trial of a human papillomavirus (HPV) peptide vaccine for women with high-grade cervical and vulvar intraepithelial neoplasia who are HPV 16 positive. *Clin Cancer Res* 6(9):3406-16 (2000)). Additionally, Van der Burg et al. have recently defined an HPV 16 E7 helper epitope (PAGQAEPDRAHYNIVTFCCKCD; SEQ ID NO:8) which effectively stimulates CD4 responses in patients with HPV 16 positive cervical lesions (van der Burg et al. Natural T-helper immunity against human papillomavirus type 16 (HPV16) E7-derived peptide epitopes in patients with HPV16-positive cervical lesions: identification of 3 human leukocyte antigen class II-restricted epitopes. *International Journal of Cancer* 91(5):612-8 (2001)).

Potential pitfalls in the development of peptide-based immunotherapy for SCCHN including: 1) peptide-induced tolerance, 2) synthetic peptide degradation, 3) limited antigenic repertoire, and 4) inadequate tools for evaluating treatment response. It is now clear that depending on the dose and timing of drug delivery, the same peptide can induce either antigen specific CTL or T cell deletion (Zinkernagel et al. Antigen localisation regulates immune responses in a dose- and time-dependent fashion: a geographical view of immune reactivity. *Immunological Reviews* 156:199-209 (1997); Mullbacher et al. In vivo administration of major histocompatibility complex class I-specific peptides from influenza virus induces specific cytotoxic T cell hyporesponsiveness. *European Journal of Immunology* 23(10):2526-31 (1993); Gallimore et al. Hierarchies of antigen-specific cytotoxic T-cell responses. *Immunological Reviews* 164:29-36 (1998); Aichele et al. T cell priming versus T cell tolerance induced by synthetic peptides. *Journal of Experimental Medicine* 182 (1):261-6, 1995)). The primary factors in determining the type of peptide-induced T cell response appear to be largely pharmacokinetic in nature (Weijzen et al. Pharmacokinetic differences between a T cell-tolerizing and a T cell-activating peptide. *J Immunol* 166(12):7151-7 (2001)). Specifically, peptides which achieve high initial tissue concentrations followed by rapid elimination tend to induce T cell deletion. Importantly, recent studies by the present inventors have clearly demonstrated that systemic peptide administration, recognized to induce T cell deletion, is preceded by T cell proliferation. In contrast, peptides that achieve gradual tissue uptake and maintain their presence preferentially induce a CTL response. In order to limit the potential for rapid systemic antigen exposure in this study, an approved human adjuvant (Montanide ISA 51), which is similar to incomplete Freunds adjuvant (IFA), may be used to regulate the temporal aspects of peptide release (Aichele et al. T cell priming versus T cell tolerance induced by synthetic peptides. *Journal of Experimental Medicine* 182(1):261-6, 1995)).

The second potential problem with synthetic peptide-based immunotherapy is the potential for proteolysis. A recent report by Amoscato et al. has clearly demonstrated that DC induces peptide degradation through both endo- and ecto-proteolysis. Ectocellular DC mediated proteolysis is primarily mediated through CD13, a molecule which appears to play a physiologic role in DC migration and extracellular antigen processing (Amoscato et al. Rapid extracellular degradation of synthetic class I peptides by human dendritic cells. *Journal of Immunology* 161(8):4023-32 (1998)). Several strategies have been designed to overcome the physiologic degradation of synthetic peptides including N and C terminal modifications and dose increases (Amoscato et al. Rapid extracellular degradation of synthetic class I peptides by human dendritic cells. *Journal of Immunology* 161(8): 4023-32 (1998)). While modification of the amino terminus has been demonstrated to reduce degradation and enhance presentation of a class II epitope, there are concerns that peptide modification can alter HLA binding (Dong et al. Modification of the amino terminus of a class II epitope confers resistance to degradation by CD13 on dendritic cells and enhances presentation to T cells. *Journal of Immunology* 164(1):129-35 (2000)). Additionally, as previously mentioned, while increased doses may enhance peptide availability for presentation, in specific settings, alteration of peptide pharmacokinetics can induce T cell deletion.

An alternative means to overcome the problem of proteolysis is through the construction of long "Trojan antigens." The present inventors have recently demonstrated that large synthetic peptides, up to 50 amino acids in length, which contain multiple epitopes linked to a translocating region of HIV TAT (RKKRRQRRR; SEQ ID NO:9) can be internalized and processed. Additionally, these peptides appear to be highly resistant to proteolysis and do not require proteosomal processing and transport by TAP, since they penetrate directly to the ER and Golgi where they form peptide/MHC complexes (Lu et al. TAP-independent presentation of CTL epitopes by Trojan antigens. *Journal of Immunology* 166(12):7063-71 (2001)). The present inventors have also established that multiple T cell epitopes can be joined together using furin-cleavable linkers (RVKR; SEQ ID NO:10), which allow the release of the individual epitopes in the Golgi, where the furin endopeptidase resides.

The third potential limiting factor for peptide-based immunotherapy is related to a defined antigenic repertoire that is HLA restricted. This factor, inherent to all peptide-based approaches, restricts patient access. Additionally, because individual peptides only have the potential to induce epitope specific CTL, the vast majority of potential tumor antigens are not targeted. In this setting, tumor down regulation of individual antigens or HLA epitopes promotes immune evasion. Recent evidence, however, suggests that this problem of epitope restriction may not be as physiologically important as was previously postulated. Specifically, it has now been clearly demonstrated that a T cell response induced against one epitope can stimulate CTL response to other target epitopes through a mechanism termed epitope-spreading (Vanderlugt et al. Epitope spreading in immune-mediated diseases: implications for immunotherapy. *Nature Reviews. Immunology* 2(2):85-95 (2002)). Using an experimental autoimmune encephalitis model, Vanderlugt et al. have demonstrated that disease progression is associated with the development of epitope specific helper T cells which are distinct from those initiating the disease. Transfer of secondary CD4 cells to naïve mice induces the disease phenotype and the disease is abrogated by blocking the secondary T cell response even though the primary T cell response remains intact (Prehn et al. Immunity to methylcolanthrene-induced sarcomas. *Journal of the National Cancer Institute* 6:769-778 (1957); McRae et al. Functional evidence for epitope spreading in the relapsing pathology of experimental autoimmune encephalomyelitis. *Journal of Experimental Medicine* 182 (1):75-85 (1995)). These data suggest that peptide-based approaches to cancer immunotherapy may indirectly stimulate multiple tumor reactive CTL against minor antigens in the presence of residual tumor.

The fourth and final limitation to peptide-based immunotherapy, is the limited number of diagnostic tools available to evaluate clinical response. Positron emission tomography (PET) in combination with systemic administration of a glucose analogue, FDG, is a relatively new imaging modality that measures metabolic activity of individual tissues. Tissues with large energy requirements, e.g. tumors, incorporate higher levels of FDG than surrounding normal tissue, allowing whole body tumor screening. Because other pathogenic processes, such as infection, can have high metabolic requirements, PET is not tumor specific. However, in patients with known tumors, PET is highly accurate for both staging head and neck cancer and identifying recurrent disease (Rege et al. Use of positron emission tomography with fluorodeoxyglucose in patients with extracranial head and neck cancers, *Cancer* 73(12):3047-3058 (1994); McGuirt et al. A comparative diagnostic study of head and neck nodal metastases using positron emission tomography. *Laryngoscope* 105((4 Pt 1)): 373-375 (1995); Laubenbacher et al. Comparison of fluorine-18-fluorodeoxyglucose PET, MRI and endoscopy for staging head and neck squamous-cell carcinomas. *Journal of Nuclear Medicine* 36(10):1747-1757 (1995); Lapela et al. Head and neck cancer: detection of recurrence with PET and 2-[F-18] fluoro-2-deoxy-D-glucose. *Radiology* 197:205-211 (1995); Bailet et al. Positron emission tomography: a new, precise imaging modality for detection of primary head and neck tumors and assessment of cervical adenopathy. *Laryngoscope* 102:281-288 (1992)). In fact, in one recent study, PET had a sensitivity of 88% compared to 25% for MRI/CT for identifying recurrent head and neck malignancy (Anzai et al. Recurrence of head and neck cancer after surgery or irradiation: prospective comparison of 2-deoxy-2-[F-18]fluoro-D-glucose PET and MR imaging diagnoses. *Radiology* 200(1): 135-141 (1996)). In patients being evaluated for response to chemotherapy, PET can accurately identify residual disease—even in some cases where initial biopsies are negative (Lowe et al. Prediction of Chemotherapy Response in Patients with Advanced Head and Neck Cancer Using [18F] Fluoro-deoxyglucose Positron Emission Tomography (FDG-PET). *Head and Neck* 19:666-674 (1997)). Recent innovations in PET technology that combine PET and CT machines into one, largely overcome the lack of anatomic detail traditionally hampering PET scan interpretation.

In view of the need for additional therapeutic options for use in the treatment of SCCHN, especially in patients with unresectable disease, the present invention provides novel Trojan antigen-based compositions and method for their use in the treatment of SCCHN. More specifically, MAGE-A3 and HPV 16-based Trojan antigen compositions, each composed of 1-2 HLA-A2.1 restricted CTL epitopes, HLA-DR helper epitopes joined together with furin-cleavable linkers and HIV TAT translocating region.

SUMMARY OF THE INVENTION

The present invention relates to Trojan antigens, and immunogenic compositions comprising the Trojan antigens. The present invention also relates to methods of generating an immune response in a subject using the Trojan antigens or immunogenic compositions. The present invention further relates to methods of treating squamous cell carcinoma of the head and neck (SCCHN) using the Trojan antigens or immunogenic compositions of the present invention.

More specifically, the present invention related to Trojan antigens, which include an isolated polypeptide comprising amino acids 1-35 of SEQ ID NO:15, an isolated polypeptide comprising amino acids 1-47 of SEQ ID NO:17, an isolated polypeptide comprising amino acids 1-21 of SEQ ID NO:19, and an isolated polypeptide comprising amino acids 1-43 of SEQ ID NO:22.

In the Trojan antigen of SEQ ID NO:19, X may be cysteine or aminobutyric acid. In the Trojan antigen of SEQ ID NO:22, each X may independently be cysteine or aminobutyric acid.

The immunogenic compositions of the present invention include immunogenic compositions comprising one or more of the following Trojan antigens: an isolated polypeptide comprising amino acids 1-35 of SEQ ID NO:15, an isolated polypeptide comprising amino acids 1-47 of SEQ ID NO:17, an isolated polypeptide comprising amino acids 1-21 of SEQ ID NO:19, wherein X may be cysteine or aminobutyric acid, and an isolated polypeptide comprising amino acids 1-43 of SEQ ID NO:22, wherein $X_6$, $X_{30}$, $X_{31}$ and $X_{33}$ are each independently cysteine or aminobutyric acid. The immunogenic compositions of the present invention further comprise a pharmaceutically acceptable carrier, diluent or adjuvant.

The methods of generating an immune response in a subject of the present invention comprising administering one or more of the following Trojan antigens to a subject in an amount sufficient to induce an immune response in said subject: a polypeptide comprising amino acids 1-35 of SEQ ID NO:15, a polypeptide comprising amino acids 1-47 of SEQ ID NO:17, a polypeptide comprising amino acids 1-21 of SEQ ID NO:19, wherein X may be cysteine or aminobutyric acid, and a polypeptide comprising amino acids 1-43 of SEQ ID NO:22, wherein $X_6$, $X_{30}$, $X_{31}$ and $X_{33}$ are each independently cysteine or aminobutyric acid. The one or more Trojan antigens may be co-administered with a pharmaceutically acceptable carrier, diluent or adjuvant.

In a preferred embodiment, the present invention includes a method of generating an immune response in a subject comprising administering the following Trojan antigens to a subject in an amount sufficient to induce an immune response in said subject: (a) a polypeptide comprising amino acids 1-47 of SEQ ID NO:17 and (b) a polypeptide comprising amino acids 1-43 of SEQ ID NO:22, wherein $X_6$, $X_{30}$, $X_{31}$ and $X_{33}$ are each independently cysteine or aminobutyric acid. The Trojan antigens may be co-administered with a pharmaceutically acceptable carrier, diluent or adjuvant.

In preferred embodiments, the one or more Trojan antigens are administered in a combined amount of between about 100 ug and about 1.5 mg, more preferably in an amount of about 1 mg.

In other preferred embodiments, the one or more Trojan antigens are co-administered with montanide, in an amount of between about 0.5 and 1.5 mL, and GM-CSF, in an amount of between about 50 and 150 ug/m$^2$.

The methods treating squamous cell carcinoma of the head and neck (SCCHN) of the present invention comprising administering to a subject in need of such treatment a therapeutically-effective amount of one of the following Trojan antigens: a polypeptide comprising amino acids 1-35 of SEQ ID NO:15, a polypeptide comprising amino acids 1-47 of SEQ ID NO:17, a polypeptide comprising amino acids 1-21 of SEQ ID NO:19, wherein X may be cysteine or aminobutyric acid, and a polypeptide comprising amino acids 1-43 of SEQ ID NO:22, wherein $X_6$, $X_{30}$, $X_{31}$ and $X_{33}$ are each independently cysteine or aminobutyric acid. The one or more Trojan antigens may be co-administered with a pharmaceutically acceptable carrier, diluent or adjuvant.

In a preferred embodiment, the method of treating SCCHN comprises administering to a subject in need of such treatment a therapeutically-effective amount of the following Trojan antigens: (a) a polypeptide comprising amino acids 1-47 of SEQ ID NO:17 and (b) a polypeptide comprising amino acids 1-43 of SEQ ID NO:22, wherein $X_6$, $X_{30}$, $X_{31}$ and $X_{33}$ are each independently cysteine or aminobutyric acid. The Trojan antigens may be co-administered with a pharmaceutically acceptable carrier, diluent or adjuvant.

In preferred embodiments, the one or more Trojan antigens are administered in a combined amount of between about 100 ug and about 1.5 mg, more preferably in an amount of about 1 mg.

In other preferred embodiments, the one or more Trojan antigens are co-administered with montanide, in an amount of between about 0.5 and 1.5 mL, and GM-CSF, in an amount of between about 50 and 150 ug/m².

The present invention also comprises the following polynucleotide molecules: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

The present invention further comprises expression vectors comprising one of the following polynucleotide molecules: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

The present invention additionally includes a host cell comprising an expression vector, wherein the expression vector comprises one of the following polynucleotide molecules: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

The present invention further includes methods of preparing a polypeptide, comprising culturing a host cell comprising an expression vector, which in turn comprises a polynucleotide molecule, under conditions promoting expression of the polypeptide encoded by the polynucleotide molecule and recovering the polypeptide from the cell culture. In preferred embodiments, the polynucleotides include: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

DETAILED DESCRIPTION OF THE INVENTION

Figure 1:
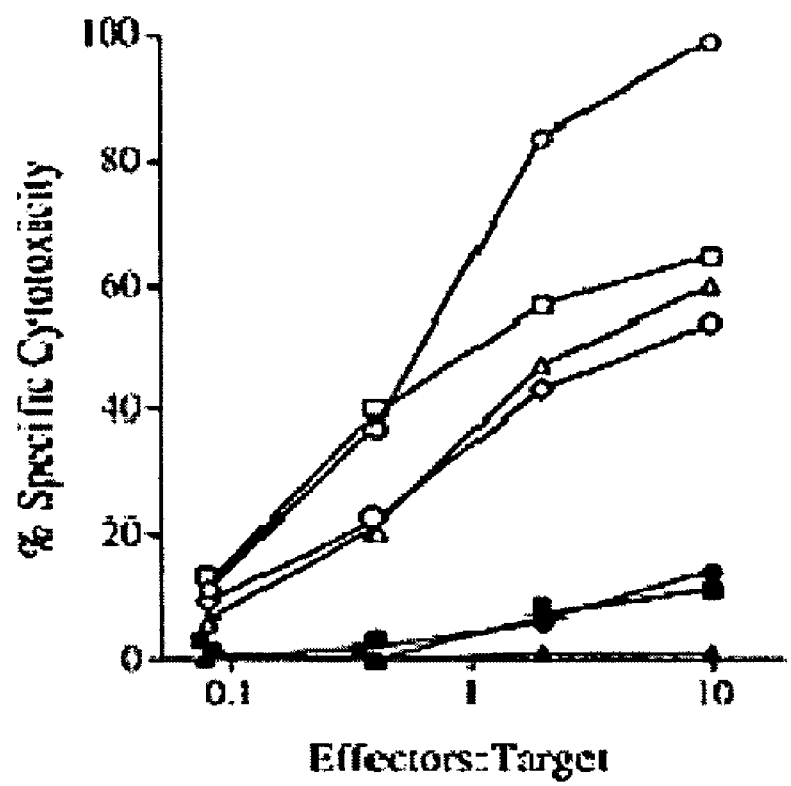
FIG. 1 is a graphical representation of the ability of a MAGE3-specific cytotoxic T lymphocyte (CTL) clone to recognize different tumor types. An MAGE3[$9_{112}$]-specific CTL clone was tested for cytotoxicity using the following targets: ○, 0.221A2.1 pulsed with MAGE3[$9_{112}$], ○, 0.221A2.1 without peptide; Δ, 624 mel (melanoma, A2⁺, MAGE3⁺); □, KATO-III (gastric Ca, A2⁺, MAGE3⁺); ◇, SW403 (colon Ca, A2⁺, MAGE3⁺); □, WiDr (colon Ca, A2⁻, MAGE3⁺); Α, 888 mel (melanoma, A2⁻, MAGE3⁻).

The present invention relates to Trojan antigens, and immunogenic compositions comprising the Trojan antigens. The present invention also relates to methods of generating an immune response in a subject using the Trojan antigens or immunogenic compositions. The present invention further relates to methods of treating squamous cell carcinoma of the head and neck (SCCHN) using the Trojan antigens or immunogenic compositions of the present invention.

Trojan Antigens

One embodiment of the present invention pertains to Trojan antigens. Trojan antigens are polypeptides comprising one or more antigenic epitopes joined together by cleavable linkers, that may be used as peptide vaccines for administration to a subject. Therapeutic peptide vaccines may be used to induce a subject's innate anti-tumor response by using antigenic epitopes derived from polypeptides expressed by the tumor cells from said subject. Trojan antigens are processed by antigen presenting cells (APC) which then display the antigenic epitopes of the Trojan antigens on their surface. Cytotoxic T lymphocytes (CTL) are activated by the APC displaying the antigenic epitopes in the context of MHC class I molecules, which then recognize and destroy tumor cells displaying the antigenic epitope in the context of a larger polypeptide.

In addition to the activation of CTL, a CD4+ helper T cell response is also activated by the APC displaying the antigenic epitopes in the context of MHC class II molecules.

In addition to the antigenic epitopes derived from tumor-expressed proteins, the Trojan antigens of the present invention may also include a transporter peptide. Transporter peptides are regions of polypeptides known to be translocated into cells without first requiring proteosomal processing and transport by TAP (transporter associated with antigen processing). Polypeptides comprising transporter peptides are internalized directly to the endoplasmic reticulum (ER) and Golgi. Inclusion of a transporter peptide in the Trojan antigens allows the Trojan antigens to be directly taken up by APC where the antigenic epitopes can form peptide/MHC complexes. Such Trojan antigens are more resistant to degradation than smaller constructs and allow simultaneous stimulation of multiple T cell populations, reducing the chance of tumor escape through the selection of antigen loss variants.

The antigenic epitopes are portions of a polypeptide, or the entire polypeptide in the case of small proteins, expressed by a tumor cell. Preferably, the polypeptide is essential for cell survival, is expressed by all cells of the tumor, is tumor specific, is a surface protein, and is a protein not expressed in the thymus nor during fetal development. After uptake and processing of Trojan antigens by antigen presenting cells, the antigenic epitopes are displayed on the cell surface in the context of MHC class I and class II molecules, which in turn induce CD8+ and CD4+ T cells, respectively. The Trojan antigens of the present invention may comprise antigenic epitopes that include CD8+ T cells alone, CD4+ T cells alone, or both CD8+ and CD4+ T cells.

While the composition of the antigenic epitopes is governed by the factors noted above, peptides homologous to antigenic epitopes may also be used in Trojan antigens to increased the spectrum of immune response generated by the Trojan antigens. Peptide homologues having at least about 90%, 91%, 92%, 93%, 94%, 95%, 96%, 97%, 98% or 99% sequence identity to a selected antigenic epitope are included in the present invention. Each reference to an antigenic epitope herein is also meant to be a reference to a peptide homologue that may be used in place of the antigenic epitope. A single Trojan antigen may comprise both a specific antigenic epitope and a peptide homologue of the specific antigenic epitope.

The antigenic epitopes of the present invention may be comprised of naturally occurring amino acids or amino acid analogues. Such analogues include those amino acids that produce cleavage-resistant peptides.

The size of the antigenic epitopes used in the Trojan antigens is not limited, though preferably the antigenic epitopes are of a size that readily forms a complex with MHC class I and class II molecules in antigen presenting cells. Preferably, the antigenic epitopes for class I molecules are peptides of between about 8 amino acids and about 10 amino acids in length. More preferably, the antigenic epitopes for class I molecules are peptides of about 9 amino acids in length. Preferably, the antigenic epitopes for class II molecules are peptides of between about 10 amino acids and about 20 amino acids in length. More preferably, the antigenic epitopes for class II molecules are peptides of about 15 amino acids in length.

The use of cleavable linkers to join antigenic epitopes (when two or more antigenic epitopes are used in a Trojan antigen) or one or more antigenic epitopes and the transporter peptide, allows the release of the individual components of the Trojan antigen upon internalization of the antigen into a cell.

Preferably, the cleavable linkers are furin-sensitive linkers which allow the components of the Trojan antigen to be separated from each other in the Golgi, where the furin endopeptidase resides. Furin is a very specific protease that recognizes a motif consisting of RX(R/K)R, where R and K are the positive-charged amino acids lysine and arginine, respectively, and X is any amino acid residue. A preferred furin linker used herein is RVKR (SEQ ID NO:10). Through the action of furin in the Golgi, the Trojan antigen is first cleaved separating the antigenic epitopes from the transporter peptide. The antigenic epitopes are then trimmed via amino- and carboxy-peptidases that are present in the ER and Golgi, until the appropriately-sized peptide is formed and binds to MHC molecules in these compartments, protecting it from further degradation. The skilled artisan will understand that any furin-cleavable linker may be used, where the first, third and fourth residues are positively charged amino acids such as lysine and arginine. Other suitable linkers will be readily apparent to the skilled artisan.

The portion of the Trojan antigen that allows direct internalization of the antigens into a cell is a transporter peptide. The transporter peptide is any peptide that allows transport of the Trojan antigen directly into a cell without first requiring proteolytic processing of the antigen. An example of a transporter peptide is the penetrin peptide of HIV TAT (Frankel et al. Cellular uptake of the tat protein from human immunodeficiency virus. *Cell* 55:1189-1193 (1988)). Several other cell penetrating sequences have been described from proteins, including the VP22 protein of herpes simplex virus (Elliott et al. Intercellular trafficking and protein delivery by a herpesvirus structural protein. *Cell* 88:223-233 (1997); Phelan et al. Intercellular delivery of functional p53 by the herpesvirus protein VP22. *Nat. Biotechnol.* 16:440-443 (1998)), the fibroblast growth factor (Lin et al. Inhibition of nuclear translocation of transcription factor NF-kappa B by a synthetic peptide containing a cell membrane-permeable motif and nuclear localization sequence. *J. Biol. Chem.* 270:14255-14258 (1995); Rojas et al. Genetic engineering of proteins with cell membrane permeability. *Nat. Biotechnol.* 16:370-375 (1998)) and the *Drosophila Antennapedia* homeodomain protein (Schutze-Redelmeier et al. Introduction of exogenous antigens into the MHC class I processing and presentation pathway by *Drosophila antennapedia* homeodomain primes cytotoxic T cells in vivo. *J. Immunol.* 157:650 (1996)).

Preferably, the transporter protein is the penetrin peptide of HIV TAT: RKKRRQRRR (SEQ ID NO:9). The transporter peptide may be coupled to either the amino- or the carboxy-terminal end of the antigenic epitopes.

In one embodiment of the invention, the Trojan antigen is based on one or more antigenic epitopes from the MAGE-A3 differentiation antigen linked to a transporter peptide. MAGE-A3 is expressed by cells of SCCHN tumors. When more than one antigenic epitope from MAGE-A3 is used, the epitopes are linked by a cleavable linker, preferably a furin-sensitive linker. In this embodiment, a cleavable linker is also used to link the selected MAGE-A3 antigenic epitopes to the transporter peptide. In a preferred embodiment, the MAGE-A3$_{112-120}$ antigenic epitope KVAELVHFL (SEQ ID NO:2) is linked to the MAGE-A3$_{271-279}$ antigenic epitope FLWGPRALV (SEQ ID NO:1) using the furin-sensitive linker RVKR (SEQ ID NO:10), to produce the linked peptide KVAELVHFL-RVKR-FLWGPRALV (SEQ ID NO:13). Upon action by furin, the linked peptide is cleaved into KVAELVHFLRVKR (SEQ ID NO:14) and FLWGPRALV (SEQ ID NO:1) in the Golgi. KVAELVHFLRVKR (SEQ ID NO:14) is then trimmed by exopeptidases into the MHC-binding peptide KVAELVHFL (SEQ ID NO:2).

In this preferred embodiment, the linked peptide KVAELVHFLRVKRFLWGPRALV (SEQ ID NO:13) is joined to the penetrin transporter peptide from HIV TAT: RKKRRQRRR (SEQ ID NO:9). In this embodiment, the Trojan antigen is KVAELVHFLRVKRFLWG-PRALVRVKRRKKRRQRRR (SEQ ID NO:15). Trojan antigens comprising the MAGE-A3$_{112-120}$ antigenic epitope linked by a furin-sensitive linker to HIV TAT penetrin (SEQ ID NO:9), or the MAGE-A3$_{271-279}$ antigenic epitope linked by a furin-sensitive linker to HIV TAT penetrin (SEQ ID NO:9), are also include in this invention.

In a further preferred embodiment of the invention, the Trojan antigen is comprised of antigenic epitopes from MAGE-A3 that induce both CD8+ and CD4+ T cells responses, i.e., the antigenic epitopes induce the formation of both class I and class II MHC complexes by APC. In this preferred embodiment, the MAGE class I antigenic epitopes MAGE-A3$_{112-120}$ (KVAELVHFL; SEQ ID NO:2) and MAGE-A3$_{271-279}$ (FLWGPRALV; SEQ ID NO:1) are linked with the class II MAGE-A3$_{149-160}$ antigenic epitope (VIF-SKASSSLQL (SEQ ID NO:5) using the furin-sensitive linker RVKR (SEQ ID NO:10), to produce the linked peptide KVAELVHFLRVKRFLWG-PRALVRVKRVIFSKASSSLQL (SEQ ID NO:16).

In this preferred embodiment, the linked peptide (SEQ ID NO:16) is joined to the penetrin transporter peptide from HIV TAT: RKKRRQRRR (SEQ ID NO:9). In this embodiment, the Trojan antigen is KVAELVHFLRVKRFLWG-PRALVRVKRVIFSKASSSLQL-RKKRRQRRR (SEQ ID NO:17).

Trojan antigens comprising the MAGE-A3$_{149\text{-}160}$ antigenic epitope linked by a furin-sensitive linker to HIV TAT penetrin (SEQ ID NO:9) are also include in this invention, as are Trojan antigens comprising the MAGE-A3$_{112\text{-}120}$ (SEQ ID NO:2) and MAGE-A3$_{149\text{-}160}$ (SEQ ID NO:5) antigenic epitopes linked to each other and to HIV TAT penetrin (SEQ ID NO:9) by a furin-sensitive linkers. Trojan antigens comprising the MAGE-A3$_{271\text{-}279}$ (SEQ ID NO:1) and MAGE-A3$_{149\text{-}160}$ (SEQ ID NO:5) antigenic epitopes linked to each other and to HIV TAT penetrin (SEQ ID NO:9) by a furin-sensitive linkers are also included in the present invention.

In a related embodiment of the invention, the Trojan antigen is based on one or more antigenic epitopes from the human papilloma virus (HPV) 16 E7 nuclear protein. HPV 16 E7 protein is a tumor rejection antigen, which is postulated to play an integral role in the development of carcinoma of the uterine cervix. When more than one antigenic epitope from HPV 16 E7 is used, the epitopes are linked by a cleavable linker, preferably a furin-sensitive linker. A cleavable linker is further used to link one or more HPV 16 E7 antigenic epitopes to a transporter peptide. In a preferred embodiment, the HPV 16 E7$_{86\text{-}93}$ antigenic epitope TLGIVXPI (SEQ ID NO:18), where X is cysteine or aminobutyric acid, preferably aminobutyric acid, is linked to the penetrin peptide sequence from HIV TAT: RKKRRQRRR (SEQ ID NO:9). In this embodiment, the Trojan antigen is TLGIVXPIRVKR-RKKRRQRRR (SEQ ID NO:19), where X is cysteine or aminobutyric acid, preferably aminobutyric acid.

In a preferred embodiment of an HPV 16 E7-based Trojan antigen, the HPV 16 E7$_{86\text{-}93}$ antigenic epitope TLGIVXPI (SEQ ID NO:18) is linked via a furin-sensitive linker to the HPV 16 E7$_{41\text{-}62}$ antigenic epitope PAGQAEPDRAHYNIVT-FXXKXD (SEQ ID NO:20), to form the linked peptide TLGIVXPIRVKRPAGQAEPDRAHYNIVTFXXKXD (SEQ ID NO:21), where each X is independently cysteine or aminobutyric acid, preferably each X is aminobutyric acid. This linked peptide (SEQ ID NO:21) is joined to the HIV TAT transporter peptide RKKRRQRRR (SEQ ID NO:9) to create the Trojan antigen TLGIVXPIRVKRPAGQAEP-DRAHYNIVTFXXKXDRKKRRQRRR (SEQ ID NO:22), where again each X is independently cysteine or aminobutyric acid, preferably each X is aminobutyric acid.

In addition to the HLA-A2 antigenic epitopes from the MAGE-A3 and HPV 16 E7 polypeptides, antigenic epitopes from these two polypeptides that associate with alternative HLA alleles may be used in the present invention. Similarly, antigenic epitopes from other tumor expressed polypeptides, such as telomerase, may be used in the present invention, both those that associate with HLA-A2, and those that associates with other HLA alleles.

The each of the antigenic epitopes, polypeptides, peptides, linkers and Trojan antigens of the present invention may be prepared based on methods well known to those of skill in the art. For example, these amino acid sequences can be produced by using recombinant DNA techniques easily identified and well known by those of skill in the art. For example, DNA molecules encoding the Trojan antigens are prepared using generally available methods such as PCR mutagenesis, site-directed mutagenesis, and/or restriction digestion and ligation. The hybrid DNA is then inserted into expression vectors and introduced into suitable host cells. Preferred expression vectors include plasmids and cosmids. An expression vector containing one or more polynucleotides encoding one or more of the Trojan antigens of this invention can be used to transfect or transform a suitable host cell (prokaryotic or eukaryotic) to produce the protein or to produce an immune response, or for some other purpose.

A recombinant virus can also be used as the expression vector. Exemplary viruses include the adenoviruses, adeno-associated viruses, herpes viruses, vaccinia, CMV, BLUE-SCRIPT (Stratagene, San Diego, Calif.), baculovirus, or an RNA virus such as a retrovirus or an alphavirus. Preferably, the retroviral vector is a derivative of a murine or avian retrovirus. The alphavirus vector is preferably derived from Sindbis or Semliki Forest Virus. All of these expression vectors can transfer or incorporate a gene for a selectable marker so that transduced cells can be identified and generated.

The viral vector can be made target specific by inserting one or more sequences of interest into the viral vector, along with another polynucleotide encoding a Trojan antigen. For example, retroviral vectors can be made target specific by inserting a polynucleotide encoding a sugar, a glycolipid, or a protein. Those of skill in the art will know of, or can readily ascertain without undue experimentation, specific polynucleotide sequences which can be inserted into the retroviral genome to allow target specific delivery of the retroviral vector containing the polynucleotides of interest.

It will be appreciated that the same techniques that are utilized to incorporate the nucleotide sequences encoding a Trojan antigen, and optionally other immunostimulatory polynucleotides, into viral gene expression vectors can be used to incorporate the sequences into live and attenuated live viruses for use as immunogenic compositions.

Construction of suitable expression vectors containing desired coding, non-coding, and control sequences employ standard ligation techniques. Isolated plasmids or DNA fragments are cleaved, tailored, and re-ligated in the form desired to construct the required plasmids. To confirm correct sequences in the plasmids constructed, the ligation mixtures can be used, for example, to transform a host cell and successful transformants selected by antibiotic resistance where appropriate. Plasmids from the transformants are prepared, analyzed by restriction and/or sequenced by, for example, by the method disclosed in Messing, et al. (Nucleic Acids Res., 9:309 (1981)), Maxam, et al. (Methods in Enzymology 65:499 (1980)), or other suitable methods which will be known to those skilled in the art. Size separation of cleaved fragments can be performed using conventional gel electrophoresis as described, for example, by Maniatis, et al. (Molecular Cloning, pp. 133-134 (1982)).

Host cells can be transformed with the expression vectors described herein and cultured in conventional nutrient media modified as is appropriate for inducing promoters, selecting transformants, or amplifying genes. The culture conditions, such as temperature, pH and the like, are those previously used with the host cell selected for expression, and will be apparent to the ordinarily skilled artisan.

Steps involved in the purification of one or more of the polypeptides, such as the Trojan antigens, of this invention include (1) solubilization of the desired protein, (2) the development of one or more isolation and concentration procedures, (3) stabilization of the protein following purification, and (4) development of a suitable assay to determine the presence of the desired protein. Various aspects of protein isolation and purification are discussed in detail in Cooper, T.

G., "The Tools of Biochemistry," John Wiley & Sons, New York, 1977. As the techniques of protein isolation and purification are notoriously well known in the art, this disclosure will refrain from discussing them in detail. Nevertheless, elements of the cited reference are summarized and discussed below.

Solubilization is required of most proteins that are to be purified, as most isolation procedures commonly used operate in aqueous solutions. In some cases, solubilization can be achieved by merely lysing a host cell within which a desired protein has been expressed. In other situations, additional steps, such as extracting the desired protein from a subcellular organelle, may be required. Osmotic lysis, grinding, the use of blenders, ultrasonic waves, presses, and other well known techniques of protein solubilization can be used with the methods disclosed herein.

There are a variety of techniques available that are well known in the art for the isolation and concentration of the proteins of this invention. These techniques include, but are not limited to, (1) differential solubility, (2) ion exchange chromatography, (3) absorption chromatography, (4) molecular sieve techniques, (5) affinity chromatography, (6) electrophoresis, and (7) electrofocusing. Each of these techniques can also be useful in the purification of a protein of this invention.

Stabilizing and maintaining a purified protein product in a functional state warrants attention to a number of different conditions such as (1) pH, (2) degree of oxidation, (3) heavy metal concentration, (4) medium polarity, (5) protease concentration, and (6) temperature. One of ordinary skill in the art would readily know which of the available techniques to use to maintain purified protein in an active form without undue experimentation.

The Trojan antigens and other polypeptides of the present invention can further be prepared using an synthetic peptide synthesizer.

Also included in the present invention are polynucleotide molecules encoding the Trojan antigens and other polypeptides, including: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

The present invention further comprises expression vectors comprising one of the following polynucleotide molecules: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

The present invention additionally includes a host cell comprising an expression vector, wherein the expression vector comprises one of the following polynucleotide molecules: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

The present invention further includes methods of preparing a polypeptide, comprising culturing a host cell comprising an expression vector, which in turn comprises a polynucleotide molecule, under conditions promoting expression of the polypeptide encoded by the polynucleotide molecule and recovering the polypeptide from the cell culture. In preferred embodiments, the polynucleotides include: a polynucleotide molecule encoding amino acids 1-35 of SEQ ID NO:15, a polynucleotide molecule encoding amino acids 1-47 of SEQ ID NO:17, a polynucleotide molecule encoding amino acids 1-21 of SEQ ID NO:19, and a polynucleotide molecule amino acids 1-43 of SEQ ID NO:22.

Immunogenic Compositions

Included within the present invention are immunogenic compositions comprising one or more Trojan antigens and a pharmaceutically acceptable carrier, diluent or adjuvant.

The immunogenic compositions of the present invention may comprise one Trojan antigen, or two or more different Trojan antigens. Embodiments of immunogenic compositions of the present invention include those comprising one or more of the specific Trojan antigens discussed herein.

In a preferred example of an immunogenic composition, the composition comprises the MAGE-A3 Trojan antigen KVAELVHFLRVKRFLWG-PRALVRVKRVIFSKASSSLQLRKKRRQRRR (SEQ ID NO:17) and the HPV 16 E7 Trojan antigen TLGIVX-PIRVKRPAGQAEPDRAHYNIVT-FXXKXDRKKRRQRRR (SEQ ID NO:22), where each X is independently cysteine or aminobutyric acid, preferably each X is aminobutyric acid, and a pharmaceutically acceptable carrier, diluent or adjuvant.

Other preferred embodiments of immunogenic compositions of the present invention comprises one or more of the following Trojan antigens: SEQ ID NO:15, SEQ ID NO:17, SEQ ID NO:19, and SEQ ID NO:22, and a pharmaceutically acceptable carrier, diluent or adjuvant. In SEQ ID NO:19, X may be cysteine or aminobutyric acid, preferably aminobutyric acid. In SEQ ID NO:22, each X may independently be cysteine or aminobutyric acid, preferably aminobutyric acid.

Preferred examples of pharmaceutically acceptable carriers, diluents and adjuvants include: (1) Dulbecco's phosphate buffered saline, pH ~7.4, containing about 1 mg/ml to 25 mg/ml human serum albumin, (2) 0.9% saline (0.9% w/v NaCl), and (3) 5% (w/v) dextrose. Other acceptable carriers, diluents and adjuvants include, but are not limited to saline, buffered saline, dextrose, water, glycerol, ethanol, and combinations thereof, buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients commonly employed in pharmaceutical compositions. The composition may be formulated as a lyophilizate using appropriate excipient solutions (e.g. sucrose) as diluents.

In addition to the immunogenic compositions comprising polypeptides, such as the Trojan antigen, included in the present invention are additional forms of immunogenic compositions. In one embodiment, nucleotide-containing immunogenic compositions are contemplated. For example, in one embodiment a Trojan antigen-encoding polynucleotide preparation including DNA or RNA that encodes an Trojan antigenic may be used for administration to a subject. Nucleotide-containing immunogenic compositions also include live viral immunogenic compositions. The viruses for use in the viral immunogenic compositions may include immunostimulatory polynucleotides.

Method of Generating an Immune Response

The present invention also includes methods of generating an immune response in a subject. The methods of generating an immune response generally involves administration of a Trojan antigen, or an immunogenic composition comprising a Trojan antigen, to a subject.

A preferred embodiment of the present invention is a method of generating an immune response in a subject comprising administering a Trojan antigen comprising amino acids 1-35 of SEQ ID NO:15 to a subject in an amount sufficient to induce an immune response in said subject.

Another preferred embodiment of the present invention is a method of generating an immune response in a subject comprising administering a Trojan antigen comprising amino acids 1-47 of SEQ ID NO:17 to a subject in an amount sufficient to induce an immune response in said subject.

A further preferred embodiment of the present invention is a method of generating an immune response in a subject comprising administering a Trojan antigen comprising amino acids 1-21 of SEQ ID NO:19 to a subject in an amount sufficient to induce an immune response in said subject. In SEQ ID NO:19, X may be cysteine or aminobutyric acid, preferably aminobutyric acid.

A equally preferred embodiment of the present invention is a method of generating an immune response in a subject comprising administering a Trojan antigen comprising amino acids 1-43 of SEQ ID NO:22 to a subject in an amount sufficient to induce an immune response in said subject. In SEQ ID NO:22, each X may independently be cysteine or aminobutyric acid, preferably aminobutyric acid.

A further preferred embodiment of the present invention is a method of generating an immune response in a subject comprising administering a (a) Trojan antigen comprising amino acids 1-47 of SEQ ID NO:17 and (b) a Trojan antigen comprising amino acids 1-43 of SEQ ID NO:22 to a subject in an amount sufficient to induce an immune response in said subject. In SEQ ID NO:22, each X may independently be cysteine or aminobutyric acid, preferably aminobutyric acid.

In each of these embodiments, the Trojan antigens may co-administered with a pharmaceutically acceptable carrier, diluent or adjuvant, in the form of an immunogenic composition.

Preferred examples of pharmaceutically acceptable carriers, diluents and adjuvants include: (1) Dulbecco's phosphate buffered saline, pH ~7.4, containing about 1 mg/ml to 25 mg/ml human serum albumin, (2) 0.9% saline (0.9% w/v NaCl), and (3) 5% (w/v) dextrose. Other acceptable carriers, diluents and adjuvants include, but are not limited to saline, buffered saline, dextrose, water, glycerol, ethanol, and combinations thereof, buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients commonly employed in pharmaceutical compositions. The composition may be formulated as a lyophilizate using appropriate excipient solutions (e.g. sucrose) as diluents.

The Trojan antigens may be administered (alone or in the context of an immunogenic composition) in a dosage containing between about 5 ug and about 100 mg of peptide, more preferably in a dosage containing between about 300 ug and about 1 mg of peptide. More preferred dosages are 300 ug, 350 ug, 400 ug, 450 ug, 500 ug, 550 ug, 600 ug, 650 ug, 700 ug, 750 ug, 800 ug, 850 ug, 900 ug, 950 ug and 1 mg of peptide.

The methods of generating an immune response as disclosed herein may also include the administration of additional compounds to augment the generation of an immune response. For example, in addition to the Trojan antigen and immunogenic compositions comprising a Trojan antigen, additional compounds may be administered before or after the Trojan antigen or immunogenic composition, or co-administered with the Trojan antigen or immunogenic composition.

Such additional compounds include Montanide and GM-CSF. Montanide (Montanide ISA-51) is a human-approved adjuvant, similar to incomplete Freunds adjuvant, recognized to regulate the temporal aspects of peptide release (Aichele et al. T cell priming versus T cell tolerance induced by synthetic peptides. *Journal of Experimental Medicine* 182(1):261-6 (1995)), used in human vaccine therapy to stimulate the immune system. GM-CSF (granulocyte macrophage-colony stimulating factor) is a cytokine involved in the growth and differentiation of myeloid and monocytic lineage cells, including dendritic cells, monocytes and tissue macrophages and cells of the granulocyte lineage.

Additional compounds include adjuvants of the Toll-like receptor family. These adjuvants include CpG-containing oligodeoxynucleotides, bacterial DNA, polyinosinic-polycytidylic acid, synthetic double-stranded RNA, synthetic IMIQUOMOD™, and RNA of viral or bacterial origin, or a viral RNA mimic.

In a preferred embodiment, both Montanide and GM-CSF are co-administered to a subject with the immunogenic composition. Montanide may be administered at a dosage of between about 0.1 mL and 10 mL, preferably at between 0.25 mL and 2 mL, more preferably at 1.2 mL. GM-CSF may be administered at a dosage of between about 5 ug/m$^2$ and 1 mg/M$^2$, preferably at between 20 ug/m$^2$ and 500 ug/m$^2$, more preferably at 100 ug/m$^2$.

Methods of Treatment

Also included in the present invention are methods of treating a subject having SCCHN. The methods of treatment generally involved administration of a Trojan antigen, or an immunogenic composition comprising a Trojan antigen, to a subject having SCCHN.

A preferred embodiment of the present invention is a method of treating SCCHN comprising administering to a subject in need of such treatment a therapeutically-effective amount of a Trojan antigen comprising amino acids 1-35 of SEQ ID NO:15.

Another preferred embodiment of the present invention is a method of treating SCCHN comprising administering to a subject in need of such treatment a therapeutically-effective amount of a Trojan antigen comprising amino acids 1-47 of SEQ ID NO:17.

A further preferred embodiment of the present invention is a method of treating SCCHN comprising administering to a subject in need of such treatment a therapeutically-effective amount of a Trojan antigen comprising amino acids 1-21 of SEQ ID NO:19. In SEQ ID NO:19, X may be cysteine or aminobutyric acid, preferably aminobutyric acid.

A equally preferred embodiment of the present invention is a method of treating SCCHN comprising administering to a subject in need of such treatment a therapeutically-effective amount of a Trojan antigen comprising amino acids 1-43 of SEQ ID NO:22. In SEQ ID NO:22, each X may independently be cysteine or aminobutyric acid, preferably aminobutyric acid.

A further preferred embodiment of the present invention is a method of treating SCCHN comprising administering to a subject in need of such treatment a therapeutically-effective amount of (a) a Trojan antigen comprising amino acids 1-47 of SEQ ID NO:17 and (b) a Trojan antigen comprising amino acids 1-43 of SEQ ID NO:22. In SEQ ID NO:22, each X may independently be cysteine or aminobutyric acid, preferably aminobutyric acid.

In each of these embodiments, the Trojan antigen maybe co-administered with a pharmaceutically acceptable carrier, diluent or adjuvant, in the form of an immunogenic composition.

Preferred examples of pharmaceutically acceptable carriers, diluents and adjuvants include: (1) Dulbecco's phosphate buffered saline, pH ~7.4, containing about 1 mg/ml to 25 mg/ml human serum albumin, (2) 0.9% saline (0.9% w/v NaCl), and (3) 5% (w/v) dextrose. Other acceptable carriers, diluents and adjuvants include, but are not limited to saline, buffered saline, dextrose, water, glycerol, ethanol, and combinations thereof, buffers, antioxidants such as ascorbic acid, low molecular weight (less than about 10 residues) polypeptides, proteins, amino acids, carbohydrates including glucose, sucrose or dextrins, chelating agents such as EDTA, glutathione and other stabilizers and excipients commonly employed in pharmaceutical compositions. The composition may be formulated as a lyophilizate using appropriate excipient solutions (e.g. sucrose) as diluents.

The Trojan antigens may be administered (alone or in the context of an immunogenic composition) in a dosage containing between about 5 ug and about 100 mg of peptide, more preferably in a dosage containing between about 300 ug and about 1 mg of peptide. A preferred dosage is between 300 ug and 1 mg. More preferred dosages are 300 ug, 350 ug, 400 ug, 450 ug, 500 ug, 550 ug, 600 ug, 650 ug, 700 ug, 750 ug, 800 ug, 850 ug, 900 ug, 950 ug and 1 mg of peptide. A physician may determine the actual dosage that will be most suitable for a subject, which may vary with the age, weight and response of the particular subject. The above dosages are exemplary of the average case. There can, of course, be individual instances where higher or lower dosage ranges are merited, and such are within the scope of this invention.

The methods of generating an immune response as disclosed herein may also include the administration of additional compounds to augment the generation of an immune response. For example, in addition to the Trojan antigen and immunogenic compositions comprising a Trojan antigen, additional compounds may be administered before or after the Trojan antigen or immunogenic composition, or co-administered with the Trojan antigen or immunogenic composition.

Such additional compounds include Montanide and GM-CSF. Montanide (Montanide ISA-51) is a human-approved adjuvant, similar to incomplete Freunds adjuvant, recognized to regulate the temporal aspects of peptide release (Aichele et al. T cell priming versus T cell tolerance induced by synthetic peptides. *Journal of Experimental Medicine* 182(1):261-6 (1995)), used in human vaccine therapy to stimulate the immune system. GM-CSF (granulocyte macrophage-colony stimulating factor) is a cytokine involved in the growth and differentiation of myeloid and monocytic lineage cells, including dendritic cells, monocytes and tissue macrophages and cells of the granulocyte lineage. Additional compounds include adjuvants of the Toll-like receptor family. These adjuvants include CpG-containing oligodeoxynucleotides, bacterial DNA, polyinosinic-polycytidylic acid, synthetic double-stranded RNA, synthetic IMIQUOMOD™, and RNA of viral or bacterial origin, or a viral RNA mimic.

In a preferred embodiment, both Montanide and GM-CSF are co-administered to a subject with the immunogenic composition. Montanide may be administered at a dosage of between about 0.1 mL and 10 mL, preferably at between 0.25 mL and 2 mL, more preferably at 1.2 mL. GM-CSF may be administered at a dosage of between about 5 ug/m$^2$ and 1 mg/m$^2$, preferably at between 20 ug/m$^2$ and 500 ug/m$^2$, more preferably at 100 ug/m$^2$.

In each of the methods described herein, the Trojan antigens and immunogenic compositions comprising the Trojan antigens may be administered to a subject by any effective, convenient manner including, for instance, administration by topical, oral, anal, vaginal, intravenous, intraperitoneal, intramuscular, subcutaneous, intranasal or intradermal routes among others. Formulations suitable for parenteral administration include aqueous and non-aqueous sterile injection solutions presented in unit-dose or multi-dose containers. It should be also understood that, in addition to the ingredients mentioned above, formulations of this invention might include other agents conventional in the art having regard to the type of formulation in question.

In each of the methods described herein, the Trojan antigens and immunogenic compositions comprising the Trojan antigens may be administered to a subject as a one-time dose, or as a series of two or more doses over prolonged periods of time. In a preferred embodiment, the Trojan antigens and immunogenic compositions of the present invention are administered as a series of four doses, with one dose administered each month for four months. In this embodiment, up to four additional doses can be administered over a further four month period. Other preferred dosing schedules include administration daily, once a week, twice a week, 3-4 times per week, weekly, twice a month and three times per month. The number of doses administered varies depending on the dosing schedule, but dosing can continue under one of the dosing schedules above for 1, 2, 3, 4, 5, 6, 7, 8, 9, 10, 11 or 12 months.

Appropriate doses for each can readily be determined by techniques well known to those of ordinary skill in the art. Such a determination will be based, in part, on the tolerability and efficacy of a particular dose using techniques similar to those used to determine proper vaccine doses. The skilled artisan will understand that combinations of the dosing schedules indicated above can also be used.

Each of the methods described herein may be practiced in vitro, in vivo, or ex vivo.

In addition to the methods for generating an immune response and methods for the treatment of SCCHN described herein, the following additional methods are included in the present invention. In one embodiment, a nucleotide sequence encoding a Trojan antigen is introduced into an exogenous organism using standard molecular biology techniques well known to those of ordinary skill in the art, such as through the use of an expression vector described herein. Exemplary molecular biology techniques are discussed in Ausubel, et al., "Short Protocols in Molecular Biology." The resulting recombinant organism can then be used as an immunogen composition in the methods described herein. In a preferred embodiment, an attenuated pathogenic organism serves as the exogenous organism.

The methods of the present invention may also be practiced using a nucleotide-containing immunogenic composition. For example, in one embodiment, an immune response may be generated in a subject, or a subject may be treated, by administering an Trojan antigen-encoding polynucleotide preparation including DNA or RNA that encodes an Trojan antigenic to the host. Preferably, the polynucleotide preparation is administered to a mucosal inductor site in the mucosal tissue of the host. Naked DNA may be administered directly to the mucosa (e.g., in saline drops) or in a recombinant gene expression vector.

Nucleotide-containing immunogenic compositions also include live viral immunogenic compositions. The viruses for use in the viral immunogenic compositions include immunostimulatory polynucleotides. Preferably, a Trojan antigen is administered through its expression by a recombinant gene expression vector.

U.S. Pat. No. 6,110,898, to Malone, et al., entitled, "DNA vaccines for eliciting a mucosal immune response" provides detailed teaching for the generation of such immunogenic compositions. In particular, Malone teaches obtaining a recombinant alphavirus vector system as described in Malone, J. G., et al., "Mucosal immune responses associated with polynucleotide vaccination", Behring Inst Mitt 98:63-72 (February 1997). DNA encoding a Trojan antigen (for example) is substituted for the lacZ gene in the vector.

Alternatively, one or more polynucleotides encoding a Trojan antigen can be introduced to an attenuated EAEC, *Salmonella* spp., *Shigella* spp., *Lactobacillus* spp., or other attenuated bacteria which is invasive for mucosal tissue, which then expresses the particular Trojan antigen encoded by the polynucleotide. The bacteria is administered to an animal to generate an immune response to the particular Trojan antigen encoded.

Pre-Screening

Preferably, the methods of the present invention are practiced on a subject that has a SCCHN tumor that expresses (a) HLA-A2 antigens and (b) either MAGE-A3 or HPV 16 E7 proteins, or (c) HLA-A2 antigens and both MAGE-A3 and HPV 16 E7 proteins.

A subject may first be typed to determine whether they are HLA-A2 positive. A subject can be typed, for example, by obtaining a blood sample, followed by PBL typing using a commercially available HLA-A detection kit (Dynal) according to manufacturer's instructions. PBLs may be also typed by PCR or flow cytometric analysis (using, for example, BB7.2 mouse anti-human HLA-A2 mAb, available from the ATCC), with known positive and negative controls (Hoffmann et al. Frequencies of Tetramer+ T Cells Specific for the Wild-Type Sequence p53264-272 Peptide in the Circulation of Patients with Head and Neck Cancer. *Cancer Research* 62(12):3521-3529 (2002)).

Tumors from patients who are HLA-A2 positive may then be evaluated for the expression of HLA-A2, MAGE-A3, and HPV16 E7. HLA-A2 expression may be evaluated by immunohistochemistry. For example, following biopsy tumors can be frozen in OCT blocks, sectioned onto glass slides, and stained with hematoxylin and eosin (H&E), anti-HLA-A2 antibody and secondary antibody, or secondary antibody alone per the DAKO EnVision+ Protocol (DAKO Corporation, Carpinteria, Calif.). Normal lung parenchyma from a known HLA-A2 positive patient may serve as a positive control.

HPV 16 E7 and MAGE-A3 detection may be performed using techniques previously published (Strome et al. Squamous Cell Carcinoma of the Tonsils: A Molecular Analysis of HPV Associations. *Clinical Cancer Research* 18:1093-1100 (2002); Kienstra et al. Identification of NY-ESO-1, MAGE-1, and MAGE-3 in head and neck squamous cell carcinoma. *Head and Neck* 25(6):457-463 (2003)). Briefly, samples may be amplified using specific primers to:

```
E6 region of HPV 16 (325 bp)
                                    (SEQ ID NO: 23)
5' - CCACAGTTATGCACAGAGCTGCAAACAACTATACAT
(HPV16-E6-140-36D)

(SEQ ID NO: 24)
5' - TTGTCCAGATGTCTTTGCTTTTCTTCAGGACACAGT
(HPV16-E6-465-36U)

MAGE-A3 primer (423 bp)
                                    (SEQ ID NO: 25)
5' - GAAGCCGGCCCAGGCTCG (SEQ ID NO: 26)
5' - GGAGTCCTCATAGGATTGGCTCC
```

The amplification reaction may be performed in 50 µl containing 10 mM Tris pH 8.3, 50 mM KCl, 2.0-mM MgCl2, 200 µM each dNTP (100 µM dUTP and 100 µM dTTP), 2.5 units Amplitaq gold (5 U/µl, Perkin Elmer), 0.1% bovine serum albumin (BSA), 19.5 µl RNase free water, 0.5 µm of each primer and 5 µl of sample DNA. PCR cycling conditions may be 95° C. for 10 min followed by 40 cycles of 95° C. for 1 min, 55° C. for 1 min, min followed by 10 min at 72° C. After amplification, 15 µl of each sample may be run on a 2% agarose gel containing 20 µg ethidium bromide in an 100 ml gel to visualize products. DNA from the Caski cell line and DNA from a known MAGE-A3 positive tumor may be used as a positive PCR control to assess the success of the amplification. PCR reagents lacking DNA (no sample added) may serve as a negative control in each PCR amplification.

EXAMPLES

Example 1

Identification of MAGE-A3 Antigenic Epitopes

Using a predictive algorithm based on the presence of MHC binding motifs, an HLA-A1-binding peptide from MAGE-A3 that induced in vitro anti-tumor CTL responses with lymphocytes from normal individuals was identified (Celis et al. Induction of anti-tumor cytotoxic T lymphocytes in normal humans using primary cultures and synthetic peptide epitopes, *PNAS USA* 91(6):2105-2109 (1994)). In addition to the HLA-A1-restricted epitope, an HLA-A2 restricted CTL epitope, which is more frequently found in the general population than HLA-A1, was identified (Kawashima et al. The multi-epitope approach for immunotherapy for cancer: identification of several CTL epitopes from various tumor-associated antigens expressed on solid epithelial tumors. *Human Immunology* 59(1):1-14 (1998)). CTL-induced by peptide MAGE-A3$_{112}$-120 (KVAELVHFLL; SEQ ID NO:2) were quite effective in recognizing tumor cells expressing MAGE-A3 antigen and HLA-A2 (FIG. 1).

Boon et al. reported the existence of another HLA-A2-restricted epitope from MAGE-A3, namely MAGE-A3$_{271-279}$ (FLWGPRALV; SEQ ID NO:1). This epitope was also efficient in inducing CTL responses to tumors expressing MAGE-A3 antigen (van der Bruggen et al. A peptide encoded by human gene MAGE-3 and presented by HLA-A2 induces cytolytic T lymphocytes that recognize tumor cells expressing MAGE-3. *European Journal of Immunology* 24(12):3038-43 (1994)).

In summary, the two HLA-A2-restricted CTL epitopes described above, MAGE-A3$_{112-120}$ and MAGE-A3$_{271-279}$, have been proven to be effective in generating cytotoxic responses against tumors expressing the MAGE-A3 antigen.

Example 2

Identification of a Promiscuous T Helper Epitope from MAGE-A3

Figure 2:
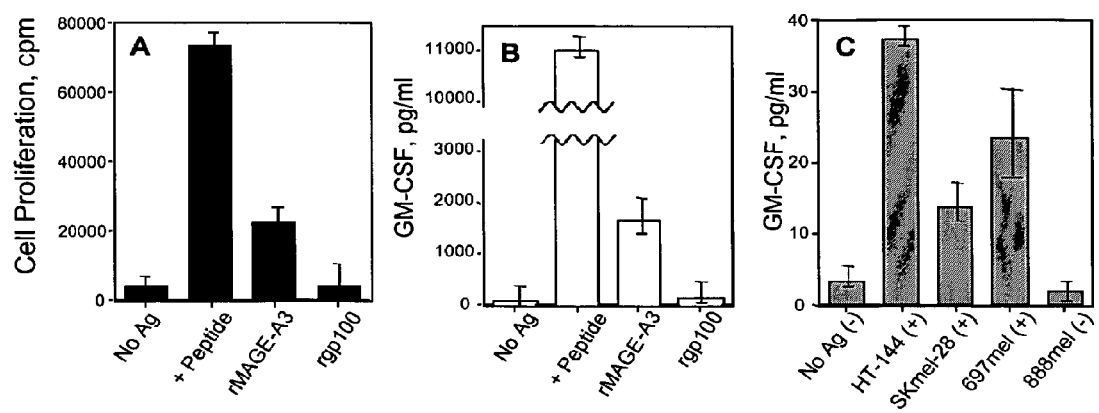
FIG. 2 is the results of experiments that demonstrated HLA-DR4-restricted HTL clone 8G9 recognizes naturally processed MAGE A3 antigen. A: Proliferative T-cell response induced by MAGE-A3$_{146-160}$ (+ Peptide), recombinant MAGE-A3 protein (rMAGE-A3) or recombinant gp100 (rgp100). B: Tissue culture supernatants from experiment described in panel A, were collected after 48 hr and the concentration of GM-CSF was measured by ELISA. C: T-cell clone 8G9 recognizes UV-irradiated melanoma cells that express MAGE-A3 (HT-144 (+), SKmel-28 (+), 697 mel (+)) via antigen cross-presentation by autologous DC. DC incubated with MAGE-A3 negative melanoma cell line (888mel (−)) did not stimulate the T-cell clone. Values shown are the means of triplicate determinations; bars, SD.

A promiscuous T helper epitope that is presented to T cells by HLA-DR4 and HLA-DR7, two of the most frequently found MHC class II alleles, was identified. Peptide MAGE-A3$_{149-160}$ (VIFSKASSSLQL; SEQ ID NO:5) was found to stimulate T helper lymphocytes that recognized recombinant MAGE-A3 protein or cell lysates from tumors expressing MAGE-A3 antigen (Kobayashi et al. Tumor-reactive T helper lymphocytes recognize a promiscuous MAGE-A3 epitope presented by various major histocompatibility complex class II alleles. *Cancer Research* 61(12):4773-8 (2001)). As shown in FIG. 2, HLA-DR4-restricted HTL clone 8G9 recognizes naturally processed MAGE-A3 antigen. A: Proliferative T-cell response induced by MAGE-A3$_{146-160}$ (+ Peptide), recombinant MAGE-A3 protein (rMAGE-A3) or recombinant gp100 (rgp100). B: Tissue culture supernatants from experiment described in panel A, were collected after 48 hr and the concentration of GM-CSF was measured by ELISA. C: T-cell clone 8G9 recognizes UV-irradiated melanoma cells that express MAGE-A3 (HT-144 (+), SKmel-28 (+), 697 mel (+)) via antigen cross-presentation by autologous DC. DC incubated with MAGE-A3 negative melanoma cell line (888 mel (−)) did not stimulate the T-cell clone. Autologous DC were incubated with irradiated melanoma cells at a 1:1 ratio for 48 hours. The antigen-pulsed DC were then mixed with HTL (at a 1:20 ratio) and 2 days later culture supernatants were collected and assayed for the presence of GM-CSF. Values shown are the means of triplicate determinations; bars, SD.

Example 3

Identification and Selection of CTL and T Helper Epitopes from HPV 16 E7

Two HLA-A2-restricted CTL epitopes and one T helper epitope were selected. The identification and description of these epitopes have been published (de Jong et al. Frequent detection of human papillomavirus 16 E2-specific T-helper immunity in healthy subjects. *Cancer Research* 62(2):472-479 (2002); Kast et al. Role of HLA-A motifs in identification of potential CTL epitopes in human papillomavirus type 16 E6 and E7 proteins. *Journal of Immunology* 152(8):3904-3912 (1994)). Furthermore, the HLA-A2-restricted CTL epitopes were shown to induce CTL responses (Jager et al. Monitoring CD8 T cell responses to NY-ESO-1: correlation of humoral and cellular immune responses. *PNAS USA* 97(9): 4760-4765 (2000); den Haan et al. Identification of a graft versus host disease-associated human minor histocompatibility antigen. *Science* 268(5216):1476-1480 (1995); Bennouna et al. Application of IL-5 ELISPOT assays to quantification of antigen-specific T helper responses. *Journal of Immunological Methods* 261(1-2):145-156 (2002)).

Example 4

Control Experiment Using Ovalbumin Antigenic Epitope

A Trojan antigen comprising the mouse CTL epitope from ovalbumin (SIINFEKL; SEQ ID NO:11), coupled to the HIV TAT transporter peptide (RKKRRQRRR; SEQ ID NO:9) via an AAA linked was preparing, yielding the RKKRRQR-RRAAASIINFEKL (SEQ ID NO:12).

Figure 3:
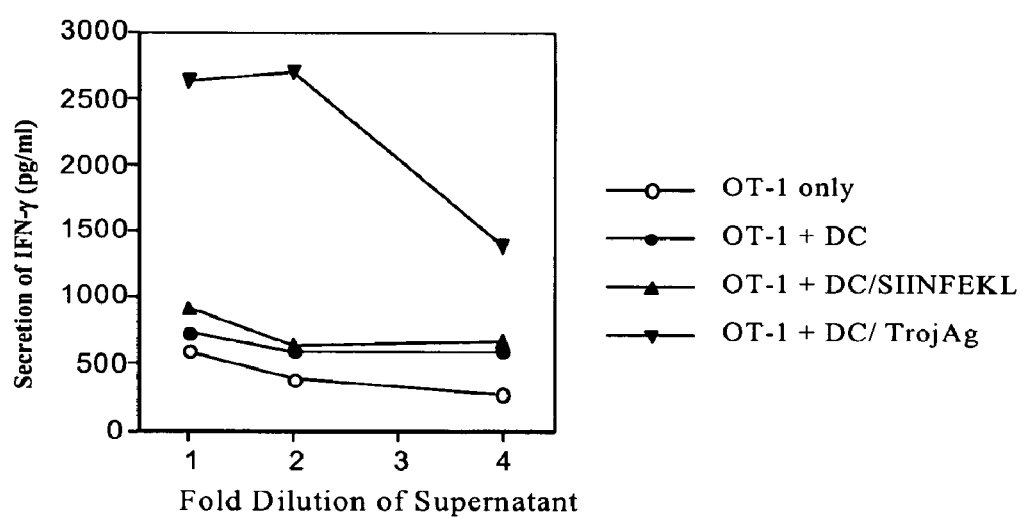
FIG. 3 is the result of an experiment where dendritic cells where pulsed with a Trojan antigen. C57/BL6 DC were pulsed with either SIINFEKL (SEQ ID NO:11) or TrojAg (RKKRRQRRRRAAASIINFEKL; SEQ ID NO:12) for 2 hours, washed three times, and then kept in 37° C. After 48 hours, the ability of peptide loaded DC to induce IFN-gamma release from OT-1 T cells was determined by ELISA. The concentration of IFN-gamma was determined at various dilutions of the supernatant that was collected after 24 hours of incubation of the DC with the OT-1 T cells.

The capacity of the ovalbumin Trojan antigen to be processed and presented by DC to OT-1 T cells specific for the SIINFEKL (SEQ ID NO:11) epitope was studied. As shown in FIG. 3, DC that were pulsed with the ovalbumin Trojan antigen remained stimulatory for T cells after a 48 hour period of incubation, while the DC that were incubated with the antigenic epitope alone had lost most of their stimulatory activity. This experiment demonstrated that pulsing the DC with Trojan antigen allowed these APC to present the epitope for a longer period of time, compared with APC pulsed with only the SIINFEKL (SEQ ID NO:11) antigenic epitope. C57/BL6 DC were pulsed with either SIINFEKL or TrojAg (RKKRRQRRRAAASIINFEKL) for 2 hours, washed three times, and then kept in 37° C. After 48 hours, the ability of peptide-loaded DC to induce IFN-gamma release from OT-1 T cells was determined by ELISA. The concentration of IFN-gamma was determined at various dilutions of the supernatant that was collected after 24 hours of incubation of the DC with the OT-1 T cells.

Example 5

HPV 16 E7 Trojan Antigens Stimulate Interferon Gamma Release from HLA-A2 T Cells To study the ability of the HPV 16 E7 Trojan antigen to stimulate functional T cell reactivity, levels of Interferon Gamma (IFN γ) release from Trojan antigen-stimulated HLA-A2 positive T cells versus IFN γ production from T cells stimulated with the constituent peptide epitopes, were determined. Briefly, freshly isolated HLA-A2 positive CD8+ (CTLs) and CD4+ (HTLs) were positively selected by Dynal magnetic bead separation (Dynal ASA). T cells were stimulated with irradiated autologous CD8−/CD4− PBLs (flow-through from the magnetic bead separation) pulsed with TLGIVXPIRVKRPAGQAEPDRAHYNIVT-FXXKXDRKKRRQRRR (SEQ ID NO:22) or the constituent HLA-A2.1 epitope TLGIVXPI (SEQ ID NO:18), where each X is aminobutyric acid, for 48 hours in 96-well Immobilon-P membrane multiscreen plate (Millipore) coated with IFN γ-specific capture antibody (BD Biosciences for IFN γ). The wells were washed, treated with Biotin-conjugated detection antibody and 3-amino-9-ethylcarbazole (AEC) for substrate development.

Figure 4:
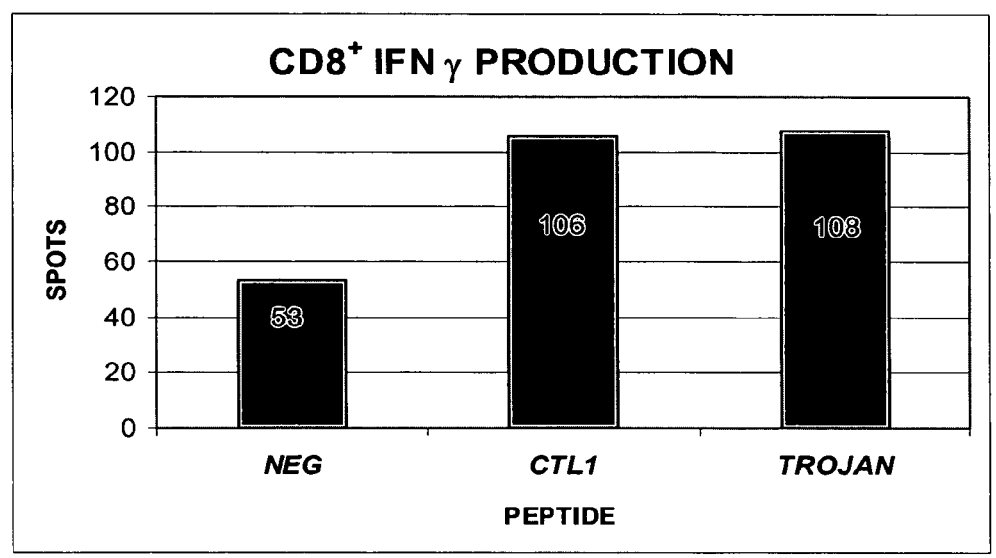
FIG. 4 shows the results of an Elispot analysis of IFN γ production by HPV 16 Trojan antigen stimulated T cells.

Spots were counted by first obtaining digitized images of the wells (performed by C.T.L. Analyzers, Cleveland, Ohio) and then analyzing these images with software purchased from C.T.L. Analyzers. The frequency of spots (250,000 cells per well) obtained with the Trojan and constituent peptides was compared and found to be equivalent at 0.02% T cell reactivity for both peptides. The results of this experiment are shown in FIG. 4.

Example 6

Expression Patterns of HLA-A2 in SCCHN

To demonstrated the ability to quantitate HLA-A2 expression on fresh SCCHN, immunohistochemical analysis was performed on five freshly isolated SCCHN, using the HLA-A2 specific mAb SB03-111 (kindly provided by Dr. Soldano Ferrone, Roswell Park Cancer Institute, Buffalo, N.Y.).

Figure 5:
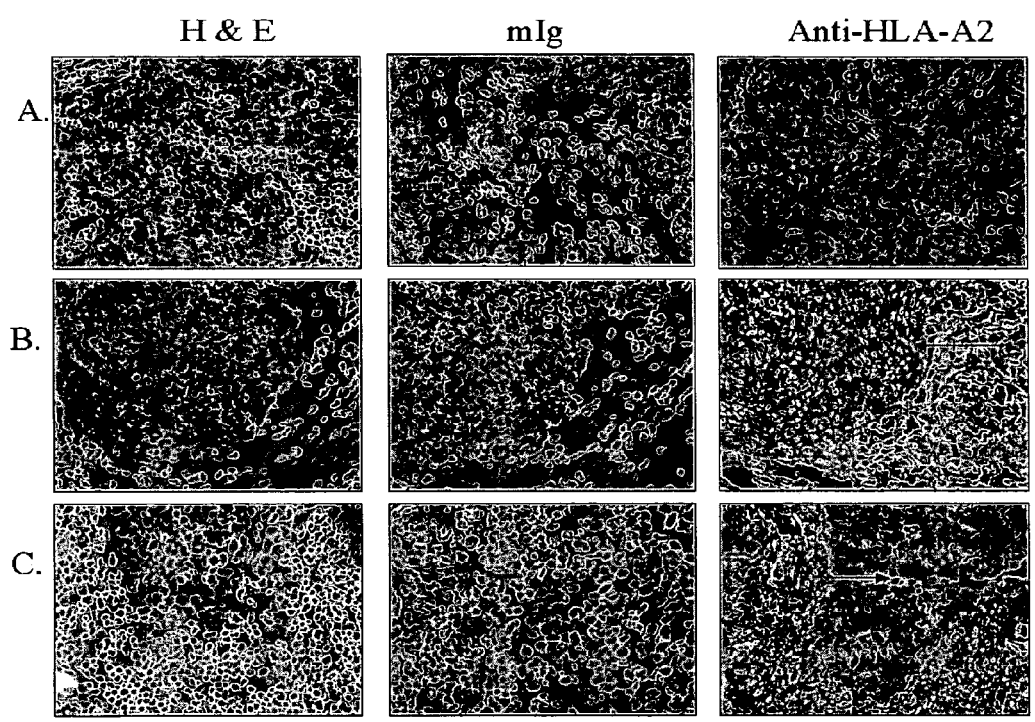
FIG. 5 shows the results of an immunohistochemical analysis of HLA-A2 expression in fresh SCCHN. Panel A: HLA-A2 negative patient with no staining of the tumor or surrounding parenchyma. Panel B: HLA-A2 positive patient with positive staining of both the tumor and surrounding parenchyma, arrows indicate tumor location. Panel C: HLA-A2 positive patient with positive staining of the parenchyma, but loss of HLA-A2 reactivity in the tumor. Specimens were stained with H&E (hematoxylin and eosin), mouse Ig control or the SB03-111 antibody.

As shown in FIG. 5, stromal tissue demonstrated a membranous cytoplasmic-staining pattern. Tissue from patients who were negative for HLA-A2 by PCR, did not display immunoreactivity to this mAb. In one HLA-A2 positive patient, the parenchyma was observed to express HLA-A2, but the tumor was negative.

The samples were prepared using freshly isolated tumors snap frozen in OCT. 5 micron sections were cut onto charged glass slides. Specimens were stained with H&E, mouse Ig control or SB03-111, using previously published techniques (Dong et al. Tumor-associated B7-H1 promotes T-cell apoptosis. A potential mechanism of immune evasion. *Nature Medicine* 8:793-800 (2002)). The optimal dilution for SB03-111 was 1/2500 (data not shown).

All documents and publications referenced herein are hereby expressly incorporated by reference in their entirety. In particular, Grant Application No. DE015324 is hereby expressly incorporated by reference in its entirety.

The invention of this application has been described above both generically and with regard to specific embodiments. Although the invention has been set forth in what is believed to be the preferred embodiments, a wide variety of alternatives known to those of skill in the art can be selected within the generic disclosure. The invention is not otherwise limited, except for the recitation of the claims set forth below.

What is claimed is:

1. A isolated polypeptide comprising amino acids 1-43 of SEQ ID NO: 22.

2. The isolated polypeptide of claim 1, wherein $X_6$, $X_{30}$, $X_{31}$ and $X_{33}$ are each cysteine.

3. An immunogenic composition comprising a polypeptide of claim 1 or 2, and a pharmaceutically acceptable carrier, diluent or adjuvant.

4. A method of generating an immune response in a subject comprising administering a polypeptide comprising amino acids 1-43 of SEQ ID NO: 22, to a subject in an amount sufficient to induce an immune response in said subject.

5. The method of claim 4, wherein said polypeptide is administered in conjunction with a pharmaceutically acceptable carrier, diluent or adjuvant.

6. The method of claim 4, wherein said polypeptide is administered in an amount of between about 100 μg and about 1.5 mg.

7. The method of claim 4, wherein said polypeptide is administered in an amount of about 1 mg.

8. The method of claim 4, wherein said polypeptide is co-administered with montanide, in an amount of between 0.5 and 1.5 mL, and GM-CSF, in an amount of between 50 and 150 μg/m$^2$.

9. A method of treating squamous cell carcinoma of the head and neck (SCCHN) comprising administering to a subject in need of such treatment a therapeutically-effective amount of a polypeptide comprising amino acids 1-43 of SEQ ID NO: 22.

10. The method of claim 9, wherein said polypeptide is co-administered with a pharmaceutically acceptable carrier, diluent or adjuvant.

11. The method of claim 9, wherein said polypeptide is administered in an amount between about 100 μg and about 1.5 mg.

12. The method of claim 9, wherein said polypeptide is administered in an amount of about 1 mg.

13. The method of claim 9, wherein said polypeptide is co-administered with montanide, in an amount of between about 0.5 and 1.5 mL, and GM-CSF, in an amount of between 50 and 150 μg/m$^2$.

14. The method of claim 4, wherein $X_6$, $X_{30}$, $X_{31}$ and $X_{33}$ are each cysteine.

15. The method of claim 9, wherein $X_6$, $X_{30}$, $X_{31}$ and $X_{33}$ are each cysteine.

* * * * *

SEQUENCE LISTING

<160> NUMBER OF SEQ ID NOS: 28

<210> SEQ ID NO 1
<211> LENGTH: 9
<212> TYPE: PRT
<213> ORGANISM: Homo sapiens

<400> SEQUENCE: 1

Phe Leu Trp Gly Pro Arg Ala Leu Val
1               5

<210> SEQ ID NO 2
<211> LENGTH: 9
<212> TYPE: PRT
<213> ORGANISM: Homo sapiens

<400> SEQUENCE: 2

Lys Val Ala Glu Leu Val His Phe Leu
1               5

<210> SEQ ID NO 3
<211> LENGTH: 14
<212> TYPE: PRT
<213> ORGANISM: Homo sapiens

<400> SEQUENCE: 3

Ala Glu Leu Val His Phe Leu Leu Leu Lys Tyr Arg Ala Arg
1               5                   10

<210> SEQ ID NO 4
<211> LENGTH: 15
<212> TYPE: PRT
<213> ORGANISM: Homo sapiens

<400> SEQUENCE: 4

Thr Ser Tyr Val Lys Val Leu His His Met Val Lys Ile Ser Gly
1               5                   10                  15

<210> SEQ ID NO 5
<211> LENGTH: 12
<212> TYPE: PRT
<213> ORGANISM: Homo sapiens

<400> SEQUENCE: 5

Val Ile Phe Ser Lys Ala Ser Ser Ser Leu Gln Leu
1               5                   10

<210> SEQ ID NO 6
<211> LENGTH: 9
<212> TYPE: PRT
<213> ORGANISM: Human papillomavirus

<400> SEQUENCE: 6

Met Leu Asp Leu Gln Pro Glu Thr Thr
1               5

<210> SEQ ID NO 7
<211> LENGTH: 8
<212> TYPE: PRT
<213> ORGANISM: Human papillomavirus

<400> SEQUENCE: 7

Thr Leu Gly Ile Val Cys Pro Ile
1               5

```
<210> SEQ ID NO 8
<211> LENGTH: 22
<212> TYPE: PRT
<213> ORGANISM: Human papillomavirus

<400> SEQUENCE: 8

Pro Ala Gly Gln Ala Glu Pro Asp Arg Ala His Tyr Asn Ile Val Thr
1               5                   10                  15

Phe Cys Cys Lys Cys Asp
            20

<210> SEQ ID NO 9
<211> LENGTH: 9
<212> TYPE: PRT
<213> ORGANISM: Human immunodeficiency virus

<400> SEQUENCE: 9

Arg Lys Lys Arg Arg Gln Arg Arg Arg
1               5

<210> SEQ ID NO 10
<211> LENGTH: 4
<212> TYPE: PRT
<213> ORGANISM: Artificial Sequence
<220> FEATURE:
<223> OTHER INFORMATION: Chemically-synthesized furin cleavable linker

<400> SEQUENCE: 10

Arg Val Lys Arg
1

<210> SEQ ID NO 11
<211> LENGTH: 8
<212> TYPE: PRT
<213> ORGANISM: Artificial Sequence
<220> FEATURE:
<223> OTHER INFORMATION: Chemically-synthesized antigenic peptide

<400> SEQUENCE: 11

Ser Ile Ile Asn Phe Glu Lys Leu
1               5

<210> SEQ ID NO 12
<211> LENGTH: 21
<212> TYPE: PRT
<213> ORGANISM: Artificial Sequence
<220> FEATURE:
<223> OTHER INFORMATION: Chemically-synthesized antigenic peptide

<400> SEQUENCE: 12

Arg Lys Lys Arg Arg Gln Arg Arg Arg Ala Ala Ala Ser Ile Ile
1               5                   10                  15

Asn Phe Glu Lys Leu
            20

<210> SEQ ID NO 13
<211> LENGTH: 22
<212> TYPE: PRT
<213> ORGANISM: Artificial Sequence
<220> FEATURE:
<223> OTHER INFORMATION: Chemically-synthesized antigenic peptide

<400> SEQUENCE: 13

Lys Val Ala Glu Leu Val His Phe Leu Arg Val Lys Arg Phe Leu Trp
1               5                   10                  15
```

```
Gly Pro Arg Ala Leu Val
        20

<210> SEQ ID NO 14
<211> LENGTH: 13
<212> TYPE: PRT
<213> ORGANISM: Artificial Sequence
<220> FEATURE:
<223> OTHER INFORMATION: Chemically-synthesized antigenic peptide

<400> SEQUENCE: 14

Lys Val Ala Glu Leu Val His Phe Leu Arg Val Lys Arg
1               5                   10

<210> SEQ ID NO 15
<211> LENGTH: 35
<212> TYPE: PRT
<213> ORGANISM: Artificial Sequence
<220> FEATURE:
<223> OTHER INFORMATION: Chemically-synthesized antigenic peptide

<400> SEQUENCE: 15

Lys Val Ala Glu Leu Val His Phe Leu Arg Val Lys Arg Phe Leu Trp
1               5                   10                  15

Gly Pro Arg Ala Leu Val Arg Val Lys Arg Lys Lys Arg Arg Gln
            20                  25                  30

Arg Arg Arg
        35

<210> SEQ ID NO 16
<211> LENGTH: 38
<212> TYPE: PRT
<213> ORGANISM: Artificial Sequence
<220> FEATURE:
<223> OTHER INFORMATION: Chemically-synthesized antigenic peptide

<400> SEQUENCE: 16

Lys Val Ala Glu Leu Val His Phe Leu Arg Val Lys Arg Phe Leu Trp
1               5                   10                  15

Gly Pro Arg Ala Leu Val Arg Val Lys Arg Val Ile Phe Ser Lys Ala
            20                  25                  30

Ser Ser Ser Leu Gln Leu
        35

<210> SEQ ID NO 17
<211> LENGTH: 47
<212> TYPE: PRT
<213> ORGANISM: Artificial Sequence
<220> FEATURE:
<223> OTHER INFORMATION: Chemically-synthesized antigenic peptide

<400> SEQUENCE: 17

Lys Val Ala Glu Leu Val His Phe Leu Arg Val Lys Arg Phe Leu Trp
1               5                   10                  15

Gly Pro Arg Ala Leu Val Arg Val Lys Arg Val Ile Phe Ser Lys Ala
            20                  25                  30

Ser Ser Ser Leu Gln Leu Arg Lys Lys Arg Arg Gln Arg Arg Arg
        35                  40                  45

<210> SEQ ID NO 18
<211> LENGTH: 8
<212> TYPE: PRT
<213> ORGANISM: Human papillomavirus
<220> FEATURE:
```

```
<221> NAME/KEY: MISC_FEATURE
<222> LOCATION: (6)..(6)
<223> OTHER INFORMATION: "X" is cysteine or aminobutyric acid

<400> SEQUENCE: 18

Thr Leu Gly Ile Val Xaa Pro Ile
1               5

<210> SEQ ID NO 19
<211> LENGTH: 21
<212> TYPE: PRT
<213> ORGANISM: Artificial Sequence
<220> FEATURE:
<223> OTHER INFORMATION: Chemically-synthesized antigenic peptide
<220> FEATURE:
<221> NAME/KEY: MISC_FEATURE
<222> LOCATION: (6)..(6)
<223> OTHER INFORMATION: "X" is cysteine or aminobutyric acid

<400> SEQUENCE: 19

Thr Leu Gly Ile Val Xaa Pro Ile Arg Val Lys Arg Arg Lys Lys Arg
1               5                   10                  15

Arg Gln Arg Arg Arg
            20

<210> SEQ ID NO 20
<211> LENGTH: 22
<212> TYPE: PRT
<213> ORGANISM: Human papillomavirus
<220> FEATURE:
<221> NAME/KEY: MISC_FEATURE
<222> LOCATION: (18)..(18)
<223> OTHER INFORMATION: "X" is cysteine or aminobutyric acid
<220> FEATURE:
<221> NAME/KEY: MISC_FEATURE
<222> LOCATION: (19)..(19)
<223> OTHER INFORMATION: "X" is cysteine or aminobutyric acid
<220> FEATURE:
<221> NAME/KEY: MISC_FEATURE
<222> LOCATION: (21)..(21)
<223> OTHER INFORMATION: "X" is cysteine or aminobutyric acid

<400> SEQUENCE: 20

Pro Ala Gly Gln Ala Glu Pro Asp Arg Ala His Tyr Asn Ile Val Thr
1               5                   10                  15

Phe Xaa Xaa Lys Xaa Asp
            20

<210> SEQ ID NO 21
<211> LENGTH: 34
<212> TYPE: PRT
<213> ORGANISM: Artificial Sequence
<220> FEATURE:
<223> OTHER INFORMATION: Chemically-synthesized antigenic peptide
<220> FEATURE:
<221> NAME/KEY: MISC_FEATURE
<222> LOCATION: (6)..(6)
<223> OTHER INFORMATION: "X" is cysteine or aminobutyric acid
<220> FEATURE:
<221> NAME/KEY: MISC_FEATURE
<222> LOCATION: (30)..(30)
<223> OTHER INFORMATION: "X" is cysteine or aminobutyric acid
<220> FEATURE:
<221> NAME/KEY: MISC_FEATURE
<222> LOCATION: (31)..(31)
<223> OTHER INFORMATION: "X" is cysteine or aminobutyric acid
<220> FEATURE:
<221> NAME/KEY: MISC_FEATURE
<222> LOCATION: (33)..(33)
<223> OTHER INFORMATION: "X" is cysteine or aminobutyric acid

<400> SEQUENCE: 21
```

Thr Leu Gly Ile Val Xaa Pro Ile Arg Val Lys Arg Pro Ala Gly Gln
1               5                   10                  15

Ala Glu Pro Asp Arg Ala His Tyr Asn Ile Val Thr Phe Xaa Xaa Lys
            20                  25                  30

Xaa Asp

<210> SEQ ID NO 22
<211> LENGTH: 43
<212> TYPE: PRT
<213> ORGANISM: Artificial Sequence
<220> FEATURE:
<223> OTHER INFORMATION: Chemically-synthesized antigenic peptide
<220> FEATURE:
<221> NAME/KEY: MISC_FEATURE
<222> LOCATION: (6)..(6)
<223> OTHER INFORMATION: "X" is cysteine or aminobutyric acid
<220> FEATURE:
<221> NAME/KEY: MISC_FEATURE
<222> LOCATION: (30)..(30)
<223> OTHER INFORMATION: "X" is cysteine or aminobutyric acid
<220> FEATURE:
<221> NAME/KEY: MISC_FEATURE
<222> LOCATION: (31)..(31)
<223> OTHER INFORMATION: "X" is cysteine or aminobutyric acid
<220> FEATURE:
<221> NAME/KEY: MISC_FEATURE
<222> LOCATION: (33)..(33)
<223> OTHER INFORMATION: "X" is cysteine or aminobutyric acid

<400> SEQUENCE: 22

Thr Leu Gly Ile Val Xaa Pro Ile Arg Val Lys Arg Pro Ala Gly Gln
1               5                   10                  15

Ala Glu Pro Asp Arg Ala His Tyr Asn Ile Val Thr Phe Xaa Xaa Lys
            20                  25                  30

Xaa Asp Arg Lys Lys Arg Arg Gln Arg Arg Arg
            35                  40

<210> SEQ ID NO 23
<211> LENGTH: 36
<212> TYPE: DNA
<213> ORGANISM: Human papillomavirus

<400> SEQUENCE: 23
ccacagttat gcacagagct gcaaacaact atacat                          36

<210> SEQ ID NO 24
<211> LENGTH: 36
<212> TYPE: DNA
<213> ORGANISM: Human papillomavirus

<400> SEQUENCE: 24
ttgtccagat gtctttgctt ttcttcagga cacagt                          36

<210> SEQ ID NO 25
<211> LENGTH: 18
<212> TYPE: DNA
<213> ORGANISM: Homo sapiens

<400> SEQUENCE: 25
gaagccggcc caggctcg                                              18

<210> SEQ ID NO 26
<211> LENGTH: 23
<212> TYPE: DNA
<213> ORGANISM: Homo sapiens

```
<400> SEQUENCE: 26
ggagtcctca taggattggc tcc                                              23

<210> SEQ ID NO 27
<211> LENGTH: 314
<212> TYPE: PRT
<213> ORGANISM: Homo sapiens

<400> SEQUENCE: 27
```

Met Pro Leu Glu Gln Arg Ser Gln His Cys Lys Pro Glu Glu Gly Leu
1               5                   10                  15

Glu Ala Arg Gly Glu Ala Leu Gly Leu Val Gly Ala Gln Ala Pro Ala
            20                  25                  30

Thr Glu Glu Gln Glu Ala Ala Ser Ser Ser Thr Leu Val Glu Val
        35                  40                  45

Thr Leu Gly Glu Val Pro Ala Ala Glu Ser Pro Asp Pro Pro Gln Ser
    50                  55                  60

Pro Gln Gly Ala Ser Ser Leu Pro Thr Thr Met Asn Tyr Pro Leu Trp
65                  70                  75                  80

Ser Gln Ser Tyr Glu Asp Ser Ser Asn Gln Glu Glu Glu Gly Pro Ser
                85                  90                  95

Thr Phe Pro Asp Leu Glu Ser Glu Phe Gln Ala Ala Leu Ser Arg Lys
            100                 105                 110

Val Ala Glu Leu Val His Phe Leu Leu Leu Lys Tyr Arg Ala Arg Glu
        115                 120                 125

Pro Val Thr Lys Ala Glu Met Leu Gly Ser Val Val Gly Asn Trp Gln
    130                 135                 140

Tyr Phe Phe Pro Val Ile Phe Ser Lys Ala Ser Ser Ser Leu Gln Leu
145                 150                 155                 160

Val Phe Gly Ile Glu Leu Met Glu Val Asp Pro Ile Gly His Leu Tyr
                165                 170                 175

Ile Phe Ala Thr Cys Leu Gly Leu Ser Tyr Asp Gly Leu Leu Gly Asp
            180                 185                 190

Asn Gln Ile Met Pro Lys Ala Gly Leu Leu Ile Ile Val Leu Ala Ile
        195                 200                 205

Ile Ala Arg Glu Gly Asp Cys Ala Pro Glu Glu Lys Ile Trp Glu Glu
    210                 215                 220

Leu Ser Val Leu Glu Val Phe Glu Gly Arg Glu Asp Ser Ile Leu Gly
225                 230                 235                 240

Asp Pro Lys Lys Leu Leu Thr Gln His Phe Val Gln Glu Asn Tyr Leu
                245                 250                 255

Glu Tyr Arg Gln Val Pro Gly Ser Asp Pro Ala Cys Tyr Glu Phe Leu
            260                 265                 270

Trp Gly Pro Arg Ala Leu Val Glu Thr Ser Tyr Val Lys Val Leu His
        275                 280                 285

His Met Val Lys Ile Ser Gly Gly Pro His Ile Ser Tyr Pro Pro Leu
    290                 295                 300

His Glu Trp Val Leu Arg Glu Gly Glu Glu
305                 310

```
<210> SEQ ID NO 28
<211> LENGTH: 98
<212> TYPE: PRT
<213> ORGANISM: Human papillomavirus

<400> SEQUENCE: 28
```

-continued

```
Met His Gly Asp Thr Pro Thr Leu His Glu Tyr Met Leu Asp Leu Gln
1               5                   10                  15

Pro Glu Thr Thr Asp Leu Tyr Cys Tyr Glu Gln Leu His Asp Ser Ser
            20                  25                  30

Glu Glu Glu Asp Glu Ile Asp Gly Pro Ala Gly Gln Ala Glu Pro Asp
            35                  40                  45

Arg Ala His Tyr Asn Ile Val Thr Phe Cys Cys Lys Cys Asp Ser Thr
        50                  55                  60

Leu Arg Leu Cys Val Gln Ser Thr His Val Asp Ile Arg Thr Leu Glu
65                      70                  75                  80

Asp Leu Leu Met Gly Thr Leu Gly Ile Val Cys Pro Ile Cys Ser Gln
                85                  90                  95

Lys Pro
```